US010590441B2

(12) United States Patent
Grassi et al.

(10) Patent No.: US 10,590,441 B2
(45) Date of Patent: Mar. 17, 2020

(54) PROCESS FOR BIOFUEL AND BIOCHEMICAL PRODUCTION, CULTURE MEDIUM AND BIOFUEL AND BIOCHEMICAL PRODUCED

(71) Applicant: API Intellectual Property Holdings, LLC, Atlanta, GA (US)

(72) Inventors: Maria Carolina de Barros Grassi, São Paulo (BR); Gonçalo Amarante Guimarães Pereira, São Paulo (BR); Theodora Retsina, Atlanta, GA (US)

(73) Assignee: GranBio Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 15/090,638

(22) Filed: Apr. 5, 2016

(65) Prior Publication Data

US 2016/0289707 A1 Oct. 6, 2016

Related U.S. Application Data

(60) Provisional application No. 62/143,558, filed on Apr. 6, 2015.

(51) Int. Cl.
*C12P 7/28* (2006.01)
*C12P 7/16* (2006.01)
*C12P 7/10* (2006.01)
*C12P 7/06* (2006.01)

(52) U.S. Cl.
CPC ............. *C12P 7/28* (2013.01); *C12P 7/065* (2013.01); *C12P 7/10* (2013.01); *C12P 7/16* (2013.01); *C12P 2203/00* (2013.01); *Y02E 50/10* (2013.01); *Y02E 50/16* (2013.01); *Y02E 50/17* (2013.01)

(58) Field of Classification Search
CPC .... C12P 7/065; C12P 7/10; C12P 7/16; C12P 2203/00; C12P 7/28; Y02E 50/10; Y02E 50/16
See application file for complete search history.

(56) References Cited

U.S. PATENT DOCUMENTS 8,389,243 B2 3/2013 Gao et al.
2009/0011484 A1 1/2009 Berlin et al.

FOREIGN PATENT DOCUMENTS

WO 201204460 A2 1/2012

OTHER PUBLICATIONS

Yamamoto et al., "Biobutanol from forest residues—a process utilizing SO2-ethanol-water fractionation and ABE fermentation", NWBC 2012, The 4th Nordic Wood Biorefinery Conference Helsinki, Finland, Oct. 23-25, 2012, p. 205-210.*
Survase et al., 2013, J Ind Microbiol. Biotechnol, vol. 40, p. 209-215.*
Yu et al., Journal of Biotechnology, 2007, vol. 129, p. 415-420.*
Shi et al., "Production of lactic acid from the mixture of softwood pre-hydrolysate and paper mill sludge by simultaneous saccharification and fermentation" Appl. Biochem. Biotechnol., Mar. 2015, vol. 175, Issue 5, pp. 2741-2754.

* cited by examiner

*Primary Examiner* — Kade Ariani
(74) *Attorney, Agent, or Firm* — O'Connor & Company; Ryan P. O'Connor

(57) ABSTRACT

The present invention relates to a process and a culture medium for biofuel and biochemical production by fermentation of lignocellulose biomass. The process describes the use of a solid-liquid mixed blend formed by solid fiber pulp, hydrolysate, and a polypeptide complex. The solid fiber pulp is partially degraded by the polypeptide complex allowing microbe immobilization and, at the same time, releasing substances that affect *Clostridium* quorum sensing pathways. The present process and culture medium allow the improvement of biofuels and biochemical production, as butanol and acetone in an industrial scale.

17 Claims, 20 Drawing Sheets

PROCESS FOR BIOFUEL AND BIOCHEMICAL PRODUCTION, CULTURE MEDIUM AND BIOFUEL AND BIOCHEMICAL PRODUCED

PRIORITY DATA

The present patent application is a non-provisional patent application claiming priority to U.S. Provisional Patent App. No. 62/143,558, filed on Apr. 6, 2015, which is hereby incorporated by reference herein.

FIELD OF THE INVENTION

The present invention relates to a process and a culture medium for biofuel and biochemical production by fermentation of lignocellulose biomass. Specifically the invention relates to a process for microbe immobilization and the releasing of substances believed to affect *Clostridium* quorum sensing pathways allowing the improvement of biofuel and biochemical production, such as butanol and acetone in an industrial scale.

BACKGROUND

Butanol is an aliphatic saturated alcohol with molecular formula of $C_4H_9OH$ used as a chemical feedstock and as an alternative fuel (Biotechnology and Bioengineering 2008, 101:209-228). As a bulk chemical, butanol is an important precursor of butyl glycol ether, butyl acetate, plasticizer as well butyl acrylate and methacrylate esters used in coating, enamels and lacquers. Besides, it is used in textile industry and applied as a solvent of a wide variety of chemicals (Environmental Technology 2013, 34: 1691-1710).

In terms of energy, butanol is a promising biofuel or biofuel additive. Compared to ethanol, butanol is less hygroscopic and less corrosive. Furthermore, it has a lower vapor pressure, higher energy content and can be blended with gasoline at higher concentrations than ethanol (Journal of Industrial Microbiology and Biotechnology 2012, 39:401-407).

Currently most of the marketed butanol is produced from petrochemical routes. However, butanol can also be produced from biological processes using *Clostridium* bacteria, which ferments carbohydrates into acetone, butanol and ethanol, called ABE fermentation (Biotechnology progress 2006, 22:673-680).

*Clostridium* is one of the largest bacterial genera and represents a heterogeneous taxonomic grouping with more than 150 species described (Practical handbook of microbiology. CRC Press, 2008) sharing a number of features as: Gram-positive staining cell wall; anaerobic metabolism; rod-shape morphology; formation of endospores; low GC content; and inability to reduce sulfate (An Introduction to the Family Clostridiaceae. In The Prokaryotes. 4th Volume., 2006). The *Clostridium* genus is widely spread being found in different habitats as soil, aquatic sediment and gastrointestinal tract (Encyclopedia of microbiology. Elsevier Inc, 2009). Many species have medical importance due to ability to produce powerful toxins and to cause severe diseases. Moreover, many individual species have a high biotechnological potential as the ability to ferment different substrates into organic acids and solvents (Clostridia. Biotechnology Set. 2nd Edition, 2008.

Fermentation production of acetone, butanol and ethanol (ABE fermentation) using *Clostridium* species was one of the largest and well-established industrial fermentation processes early in $20^{th}$ century. ABE fermentation started during World War I, when acetone demand increased drastically for the manufacture of munitions. During this time, butanol was an unwanted by-product of the fermentation, however afterwards butanol requirement increased and its production became one of largest industrial fermentation processes (Current Opinion in Biotechnology 2011, 22:634-647). Nevertheless, by 1960s fermentative production of butanol had lost its competitiveness due to high cost of raw material also used in animal feed and due to fast growing of the petrochemical industry, which produced butanol in a cheaper way than biological process. (Applied microbiology and biotechnology 2000, 54:162-167).

Recent progress in biotechnology field combined with increasing demand for the use of renewable sources and the high crude oil price have renewed the interest in butanol fermentation for use as chemical and biofuel (Bioresource Technology 2008, 99:5915-5922). However, for the restoration of ABE fermentation as an economically feasible industrial process some challenges must be overcome as the high cost of substrate, the low butanol yield, the low productivity and the high cost of product recovery (Journal of Industrial Microbiology and Biotechnology 2012, 39:401-407). Therefore, in order to improve the fermentation process different approaches are being developed as the use of alternative substrates, optimization of the fermentation process and metabolic engineering of *Clostridium* species (Current Opinion in Biotechnology 2011, 22:634-647).

Lignocellulose is the most abundant and cheapest renewable source and it does not compete with food products used in animal and human nutrition. Furthermore, this substrate is recognized as having great potential as a carbon source in fermentation (Journal of Industrial Microbiology and Biotechnology 2012, 39:401-407; Current Opinion in Biotechnology 2011, 22:331-336).

However, to be used as a substrate the lignocellulosic material should be processed and hydrolysed in order to break its complex structures, majority cellulose and hemicellulose, into fermentable sugars, like hexoses and/or pentoses, preferably glucose and/or xylose (Applied microbiology and biotechnology 2000, 54:162-167). Hydrolysate is liquid or solid material resultant from the pre-treatment and/or hydrolysis process of the lignocellulosic material. Besides high sugar concentration, as glucose, xylose and arabinose, the hydrolysate may comprise a wide range of toxic compounds, including weak acids, furans and phenolic compounds that can inhibit the fermentative microbes metabolism, and may become a possible barrier in the use of such material in the solvents and biofuels process (Journal of Industrial Microbiology and Biotechnology 2012, 39:401-407).

Clostridia are able to metabolize simple and complex carbon chains such as pentoses, hexoses, $CO_2$ and CO (Bioresource Technology 2012b, 123: 653-663), confirming the potential use of several types of sugars present in lignocellulosic material. Many studies describe that the *Clostridium* fermentation using lignocellulosic material has not a high solvent yield and productivity (Biotechnology progress 2006, 22:673-680; Bioprocess and Biosystems Engineering 2007, 30:419-427; Biomass and Bioenergy 2010, 34: 559-565; Biomass and Bioenergy 2010, 34: 566-571), however, this fact is not related to the use of lignocellulosic material. The state of the art for other substrates different than hydrolysate also is limited to low solvent yield and productivity, which can be explained by the accumulation of produced solvents and toxic compounds that causes the inhibition of growth and fermentation.

Butanol is the most toxic solvent for Clostridia. Even low concentrations of butanol (7-13 g L$^{-1}$) can be responsible for almost 50% of bacteria metabolism inhibition considering its growth rate and substrate consumption when compared to the *Clostridium* growing in a culture media without solvent or toxic products (Biotechnology and bioengineering 2008, 101:209-228).

This explanation supports one of most difficult challenges in the industrial ABE fermentation: the low yield and low productivity of solvents due to the toxicity of solvents to the *Clostridium*, which has its metabolism interrupted by lower concentration of solvents or any other type of toxic compounds comprised in the culture media, resulting in low concentration of produced solvents or fuels (Trends in biotechnology 1995, 13:259-264; Biotechnology and bioengineering 2008, 101:209-228).

Therefore, in order to produce large amount of solvents or biofuels, some current processes continuously recover produced solvents, leaving a culture media less toxic for *Clostridium*, which would allow higher growth rate, and consequently higher yield and solvent and/or biofuel productivity, when compared with the process without the recovering step. Otherwise, the solvent recovery step makes the process become more expensive (Food and Bioproducts Processing 2000, 78:139-144) and, consequently, less industrially competitive.

Many strategies using metabolic engineering and adaptive evolution are also being developed to improve the strain tolerance (Food and Bioproducts Processing 2000, 78:139-144). However, these strategies have shown to be expensive, laborious, time-consuming and frequently the increase of solvent production can be achieved only by using alternative culture conditions or fermentation procedures.

In this context, fermentation using immobilized cells has shown one of the most promising solutions to achieve higher cell density and then greater productivities and yields. Additionally, many studies have already demonstrated the potential of this technology to obtain especially high butanol productivities.

Friedl et al. (Biotechnology and Bioengineering 1991, 38:518-527) have studied an ABE fermentation integrated with product removal by using cells of *Clostridium acetobutylicum* immobilized onto a packed bed of bonechar coupled with pervaporation process. The packed bed consists of a column of packed bonechar where cells are immobilized and through which the substrate flows. However, during the fermentation, a substantial amount of $CO_2$ is produced by the fermentative microorganism and, considering that the packed bed has no flexibility, there is a risk of disrupting the matrix since there is not enough space for the released $CO_2$. A solvent productivity of 3.5 g h$^{-1}$ and a solvent yield of 0.39 g g$^{-1}$ were achieved using these apparatus.

Huang et al. (Biotechnology for Fuels and Chemicals 2004, 115:887-898) reported a butanol productivity of 4.6 g L$^{-1}$ h$^{-1}$ and a yield of 0.42 g g$^{-1}$ at a dilution rate of 0.9 h$^{-1}$ from continuous culture of *Clostridium acetobutylicum* cultivated in a fibrous bed bioreactor. This apparatus comprises a wound cotton matrix where *Clostridium* cells are immobilized and it is supported by a stainless steel mesh into the bioreactor. The open spaces between wound layers of the matrix provide the scape of $CO_2$, which was a limitation of Friedl's (1991) technology. However, this technology requires relatively high liquid flow into the bioreactor to reduce limitations of the mass transport through the matrix layers.

Chen et al. (Biotechnology and Bioprocess Engineering 2013, 18:234-241) immobilized Clostridia cells in a pretreated cotton towel and reported an increasing of 28.3% of butanol yield using immobilized cells when compared with a method with cell suspension. To immobilize the Clostridia cells by adsorption, the cotton towels had to be pretreated as described forward: boiled in water, dried in an oven, soaked in a polyethyleneimine solution with pH regulation, washed in distilled water, soaked in glutaraldehyde, prepared with phosphate-buffer saline (PBS), washed with distilled water, dried in oven and stored. This pretreatment is necessary to the cotton towel surface become much rougher and easier to adsorb the cell. The method described by Chen suggested that immobilization process is a possible method to improve butanol yield and productivity due to a probable increased tolerance to butanol, however, the immobilization method has shown complicated and much laborious when compared to the method described in the present invention.

US2013/0211143A1 discloses an apparatus for producing organic solvents and alcohols that comprises a cell-retaining cellulosic matrix in form of sheet, mat or strip to microbe immobilization and consequently for save their biological activities for at least 14 days. The apparatus comprises a chromatography column (bio-column) filled with water, saturated cellulosic fibers and supported by a plastic net. The spruce cellulosic fibers are rolled together into a tubular form with a plastic net and inserted into column. The column is sterilized overnight using ethanol. Actively growing and producing Clostridia cell mass is loaded into the bio-column by pumping cell suspension with a high flow rate through the matrix. After the bio-matrix was saturated with cells the loading stops and the substrate solution feeding is initiated from the separate substrate bottle. The bio-column is part of a complex amount of devices for controlling growth conditions of microbe cells, fermentation, for recovering the solution that comprises the organic solvents, and for recovering the microbe cells.

CN102952745B discloses a method and an apparatus for butanol production comprising a series of successively tank fermentation. The first tank is a producing acid-immobilized reactor, the second one is a butanol-immobilized reactor and the third one is a product collection tank. The fixed reactor could be a packed bed, a fluidized bed or fiber and the immobilization medium consists of agricultural straw after treatment with activated carbon, fiber and any of a corncob.

CN87103534A discloses a method for acetone and butanol production using immobilized *Clostridium acetobutylicum* and a starch material. The cells are immobilized on a porcelain ring and the method shows efficient performance and allows continuous fermentation. WO 1981001012 A1 discloses a method for production of solvents by immobilized non-growing cells of *Clostridium*. The cells can be enclosed in a polymeric material or adsorbed in a solid material or chemically bound in a solid carrier and requires the addiction of butyric acid to increase the yield of butanol.

It is important to consider that all the current cell immobilization technologies present a physical retention of the cells support matrix into an apparatus, facilitating separation of the cells from their products, which are toxic for them and reduces its metabolism, consequently reducing solvents and fuels yield. The current technologies also allow smaller bioreactor volumes due to high productivity and minimum nutrient depletion and product inhibition (Microbiological Reviews 1986, 50:484-524).

Another import disadvantage regarding to cell immobilization into a matrix is the gas production during the fermentation which leads to the accumulation of bubbles into the apparatus making the matrix floats and, consequently, taking the immobilized cell out the culture media. All these issues can affect the mill economic competitiveness because of the difficulty and high cost of maintenance, sterilization and replacement of immobilized bioreactor at large scale.

On the other hand, a second strategy that is described in the state of the art to improve butanol production is based on the quorum sensing system. This system allows the bacterium communication and synchronizes some physiological processes on a population scale by synchronizing gene expression (Annu Rev Cell Dev Biol. 2005; 21:319-46; Annu Rev Genet. 2009; 43:197-222).

The quorum sensing mechanism is mediated by extracellular signaling molecules, the autoinducers, whose concentration increases according to bacteria population density. Autoinducers are produced and released by quorum sensing bacteria, which are able to notice a critical threshold concentration of these molecules in the culture medium and modify the global gene expression. Gram-negative bacteria usually use acyl-homoserine lactone (AHL), while Gram-positive bacteria mostly use oligopeptides as the signaling molecules (Applied Microbiology and Biotehnology 2010, 87: 913-923). Usually, each bacterial species produces and responds to an exclusive autoinducer signal. In general, in Gram-negative bacteria, the autoinducers are specific specie and constituted by a variation of the homoserine lactone core. However, in Gram-positive bacteria these molecules are not variations of a single core, each species produces a peptide signal with a unique sequence. Moreover the quorum sensing receptors in Gram-positive bacteria are histidine kinase proteins with low homology in their transmembrane ligand, which defining their specificity (Annu Rev Genet. 2009, 43: 197-222). Although the inducing molecules are unique for each species, quorum sensing system also allows interspecies cell-to-cell communication and even the prokaryotes and eukaryotes communication. Many studies described the quorum sensing inducer, named AI-2, related to interspecies communication, since both Gram-positiva and Gram-negative bacteria sense and respond to this molecule (Current Opinion in Microbiology 2003, 6: 191-197). Other studies reported the production of molecules by plants that appear to mimic the activities of autoinducers and affect some bacteria behaviors regulated by quorum sensing. Among the species of higher plants reported for producing substances analogues to AHL autoinducers are pea, crown vetch, rice, soybean, tomato and *Medicago truncatula* (The American Phytophatological Society 2003, 16: 827-834).

Although the main focus of quorum sensing studies are defense mechanism and pathogenicity of bacteria, some researchers describe the role of this system during the fermentative metabolism emphasizing its importance for the production of chemicals. Houdt et al. (FEMS Microbiology Reviews 2007, 4: 407-424) reported that butanediol fermentation is regulated by AHL-mediated quorum sensing in *Aeromonas hydrophila* AH-1N, since disruption of AHL production by gene knockout blocked the bacteria growth and butanediol production. Moreover, the addition of synthetic AHL similar to the one produced by *A. hydrophila* can restore the butanediol fermentation.

Kosaka et al. (Bioscience, Biotechnology and Biochemistry 2007, 71:58-68) characterized the sol operon, which contains the genes related to solvents production, in *Clostridium saccharoperbutylacetonicum* N1-4 and suggested that its transcription, and consequently the solvent production, could be regulated by quorum sensing mechanism. A *C. saccharoperbutylacetonicum* degenerated strain restored its ability to produce solvents when it was cultivated with a fraction of the supernatant recovered from a wild-type culture thereby suggesting the presence of autoinducers in the supernatant and the probably regulation of sol operon by quorum sensing-like signal.

US 2015/0031102 A1 discloses a method for increasing the amount of butanol produced by *Clostridium* spp. The method comprises the identification of quorum sensing autoinducers in Gram-positive bacteria and their use in a culture medium to improve butanol production. The ethanol production by *Zymomonas mobilis* is up regulated in the presence of autoinducers, i.e. molecules related to quorum sensing. Based on this result, the U.S. Pat. No. 8,163,526 B2 discloses a method for increasing the production of ethanol by *Zymomonas* spp. using autoinducer-2 molecules.

Even though quorum sensing shows up as a promising technology for increased fuel and biochemical production by *Clostridium*, it is still a complex technology to be applied in a large scale. When it comes to Gram-positive bacteria, which quorum sensing occurs mainly by the action of oligopeptides, the main problem regards the fact that these oligopeptides act specifically from species to species and have formed by small combination of amino acids, making them too difficult to be identified by bioinformatic methodology of gene prediction.

In view of the aforementioned needs in the art, improvements are clearly required to manage and increase the solvent production during the fermentation of lignocellulosic biomass by *Clostridium* species.

SUMMARY OF THE INVENTION

The present invention describes a process for solvent production with efficient industrial performance in converting sugars contained in lignocellulosic biomass into biofuel and/or biochemical, such as acetone, n-butanol and ethanol (collectively referred to herein as "solvent" or "solvents"). The herein described process allows the production of solvents with high yield and productivity by immobilized cells and earlier inducing of the quorum sensing system during batch fermentation.

In the present process, the lignocellulosic material is in a first step (1) submitted to a pulping process, allowing the removal of the lignin portion from the lignocellulosic biomass, retaining mostly the solid cellulosic portion.

In the second step (2) of the present invention, fiber pulp, e.g. an amount of the fiber pulp obtained in step (1), and/or an additional amount of lignocellulosic biomass is submitted to a hydrolysis process, releasing monomeric sugars, such as hexoses and pentoses, which are further metabolized by fermentative microbes for biofuel or biochemical production.

The third step (3) involves putting together the hydrolysate obtained on the step two (2) with the cellulosic fiber pulp obtained in the step one (1) and mixing these components. The resultant solid-liquid mixed blend is part of the culture medium used in the present process.

The amount of hydrolysate added to the culture medium is determined proportionally by the ratio of pulp mass concentration to the sugar concentration present in the hydrolysate. In other words, the mass quantity of cellulosic fiber pulp that shall be added to the hydrolysate is at least about 2 to 20 times smaller (g) than the free sugar concentration available into the culture medium.

The fourth step (4) of the present process regards the addition into the culture medium of polypeptides with cellulase and/or hemicellulase activity, as well the possible addition of at least one polypeptide having one or more of the following possible activities: cellulase and/or xylanase, beta-xylosidase, hemicellulase, carbohydrate-esterase, pectinase, protease, catalase, laccase, peroxidase, H2O2-producing enzyme, oxidoredutase, expansin, swollenin, or a mixture thereof for example cellobiohydrolase I and/or II, endoglucanase I and/or II, and betaglucosidase activity. The complex containing the polypeptides with cellulase and/or hemicellulase activities, as well other polypeptides having at least one among these activities, is herein referred to as "polypeptide complex".

The fifth step (5) concerns the addition of the fermentative microbes into the culture medium. The microbe is a wild type, a mutant type or a genetically modified type selected from the group of *Clostridium* species.

The sixth step (6) regards the use of the culture medium and microbes (described from steps 1 to 5) to start a regular batch fermentation where the cellulosic fiber pulp previously degraded by the action of the polypeptide complex works as matrix to allow the *Clostridium* immobilization. Therefore, considering that the partly degraded pulp itself is able to immobilize the *Clostridium* cells, no additional apparatus is necessary to support the immobilization matrix.

Additionally, the batch fermentation made by using the previously described culture medium, which is supplemented with cellulosic fiber pulp and the polypeptide complex, allows not only the *Clostridium* immobilization, but also favors cell growth causing an increase of cell concentration, allowing a reduced number of fermentation tanks to reach high cell biomass concentration.

The nutrients released in the culture medium by the partial degradation of the cellulosic fiber pulp consists of monosaccharides, oligosaccharides, organic acids, phenolic compounds, salts and/or peptides from plant cellular components, comprising components analogous to the autoinducers compounds, related to quorum sensing system, that are naturally released by bacteria cells and that starts the quorum sensing process. In some embodiments, the nutrients analogous to the autoinducers are released into the medium in a constant and homogenous way during the partial pulp degradation by the polypeptide complex. At the time these nutrients reach high enough concentration, they start the bacterial quorum sensing phenomenon, activating genes responsible by the solventogenesis and allowing the increase of solvent production.

Both together, immobilization and quorum sensing, promote the improvement of the fermentation performance and solvent production by overcoming some of the main technical problems of ABE fermentation: the low productivity and low yield of solvents. The present technology also allows the solvent production process to be industrially efficient and easily scalable.

After solvent production the seventh (7) step of the present process comprises the optional separation and recovering of the produced solvent.

BRIEF DESCRIPTION OF THE FIGURES

FIG. 1(*b*) represents total solvents production in the same conditions as described previously. Total solvent production (g/L) is represented in the vertical axis while time (h) is represented in the horizontal axis.

In FIG. 2(*a*) it is possible to observe the total sugar consumption (g/L), represented in the vertical axis, while time (h) is represented in the horizontal axis. In FIG. 2(*b*), is possible to observe the butanol production (g/L) in the vertical axis, by time (h) in the horizontal axis. In FIG. 2(*c*) it is possible to observe the acetone production (g/L), represented in the vertical axis, while time (h) is represented in the vertical axis. In the FIG. 2(*d*) it is possible to observe the total solvent production (g/L) represented in the vertical axis, while time (h) is represented in the horizontal axis.

In FIG. 3(*a*) it is possible to observe the total sugar consumption (g/L), represented in the vertical axis, while time (h) is represented in the horizontal axis. In FIG. 3(*b*), is possible to observe the butanol production (g/L) in the vertical axis, by time (h) in the horizontal axis. In FIG. 3(*c*) it is possible to observe the acetone production (g/L), represented in the vertical axis, while time (h) is represented in the vertical axis. In the FIG. 3(*d*) it is possible to observe the total solvent production (g/L) represented in the vertical axis, while time (h) is represented in the horizontal axis.

In FIG. 4(*b*), is possible to observe the butanol production (g/L) in the vertical axis, by time (h) in the horizontal axis. In FIG. 4(*c*) it is possible to observe the acetone production (g/L), represented in the vertical axis, while time (h) is represented in the vertical axis. In the FIG. 4(*d*) it is possible to observe the total solvent production (g/L) represented in the vertical axis, while time (h) is represented in the horizontal axis.

DETAILED DESCRIPTION OF EMBODIMENTS OF THE INVENTION

Figure 1A:
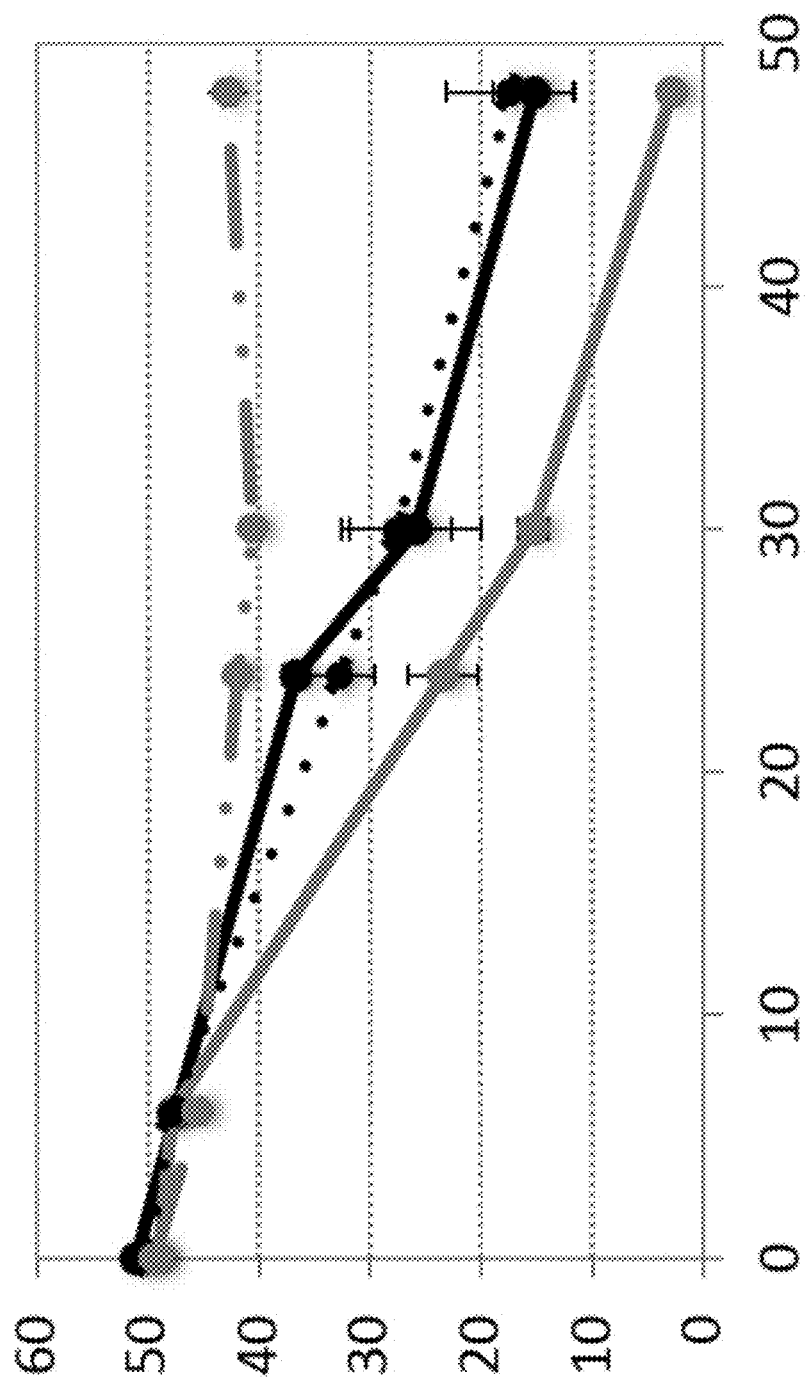
In FIGS. 1(*a*), 1(*b*) microbes were inoculated in four different culture media: (1) Control, comprising only the hydrolysate ( ——— ); (2) culture medium comprising only the hydrolysate supplemented with pulp from Aspen wood ( –--– ); (3) culture medium comprising only the hydrolysate supplemented with the polypeptide complex) ( ······· ), and (4) culture medium comprising hydrolysate supplemented with the cellulosic fiber pulp from Aspen wood and the polypeptide complex ( ▬▬▬ ). The sugar consumption can be observed in the FIG. 1(*a*) and it is represented in grams per Liter (g/L) in the vertical axis, while time in hours (h) is represented in the horizontal axis.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

The present invention describes a process for solvent production with efficient industrial performance in converting sugars contained in lignocellulosic biomass into biofuel and/or biochemical, such as acetone, n-butanol and ethanol.

The process described herein allows the production of solvents with high yield and productivity by immobilized cells and earlier inducing of the quorum sensing system during batch fermentation. Note that "batch" fermentation should be construed herein to include traditional batch fermentation, semi-batch fermentation, fed-batch fermentation, or semi-continuous fermentation.

The process for lignocellulosic biomass converting into biofuels and/or biochemical is presented in this document described in seven steps as detailed below.

This document herein specifies lignocellulosic biomass as all the lignocellulosic material naturally found as a component of the algae and plant cell wall, which is substantially compounded by polysaccharides as sugar and can be used as carbon source for fermentation. This includes all available material such as cellulose obtained from agriculture crop residues or derivatives, hardwoods, or softwoods, but not restricted to them.

In some embodiments of the present process, the lignocellulosic material is in a first step (1) submitted to a pulping process. The aim of the pulping treatment is allowing the removal of the lignin portion from the lignocellulosic biomass, retaining mostly the cellulosic portion, which is rich in hexoses. The solid portion that remains from the lignocellulosic biomass after the pulping process is the resultant material, herein referred to as "fiber pulp" or "pulp."

In one embodiment, the lignocellulosic biomass is submitted to a pulping process by a treatment that uses ethanol, water and sulfur dioxide ($SO_2$) cooking, such as in AVAP® fractionation of biomass (see, for example, U.S. Pat. No. 8,030,039). Other technologies, e.g, kraft, stone groundwood, mechanical refiner, thermomechanical pulping, defibrated or exploded pulping, and recycled paper can also be used for the lignocellulose pulping. It is relevant to affirm that in the present process, the method for achieving the fiber pulp is not regarded as critical.

In the second step (2) of the present invention, fiber pulp, e.g. an amount of the fiber pulp obtained on step (1), and/or an additional amount of the lignocellulosic biomass, is submitted to an hydrolysis process, which allows the release of monomeric sugars, such as hexoses and pentoses (e.g. glucose and xylose). The released monomeric sugars are further metabolized by fermentative microbes for the biofuel or biochemical production.

In one embodiment, the hydrolysis is carried out by the action of peptides with cellulases and/or hemicellulases activity, which act as hydrolytic enzymes and convert the complex sugars, as cellulose and hemicellulose, from the cell wall into monomers. This sort of pre-treatment is the enzymatic hydrolysis and, considering there are other hydrolysis technologies (e.g. acid hydrolysis, hydrothermal, etc.), the present process is not restricted to the enzymatic one. It is relevant to affirm that the hydrolysis method is not limited in the present process.

The third step (3) of the present process involves putting together the hydrolysate obtained in the step two (2) with the fiber pulp obtained in the step one (1) and mixing these components together. The resultant solid-liquid mixed blend is part of the culture medium used in the present process.

The amount of hydrolysate added to the culture medium is determined by the amount of free sugars, mainly glucose and xylose, which the hydrolysate can provide to the medium. In this case, the preferable concentration of sugar varies between at least from 20 to 80 grams of sugar per Liter of hydrolysate (g/L), or from 25 to 75, or from 30 to 70, or 35 to 65, or 40 to 60, or 45 to 55 grams of sugar per Liter of hydrolysate.

On the other hand, the amount of fiber pulp that must be added to the culture medium is defined proportionally by the ratio of pulp mass concentration to the sugar concentration present in the hydrolysate. In other words, the mass quantity of fiber pulp that should be added to the hydrolysate is at least about 2 to 20 times smaller (g) than the free sugar concentration available into the culture medium.

In other words, if the culture medium has 80 g/L of sugars that have come from the hydrolysate, it is preferred to add approximately from about 8 to 40 g/L of fiber pulp to comprise the culture medium of the present invention.

The fourth step (4) of the present process regards the addition of polypeptides, which have cellulases and/or hemicellulases activity, into the culture medium. Additionally, besides the addition the of polypeptides with cellulase and/or hemicellulase activity, the present process also comprise the possible addition in the culture medium of at least one polypeptide presenting one or more of the following activities: cellulolytic and/or xylanase, beta-xylosidase, carbohydrate-estarase, pectinase, protease, catalase, laccase, peroxidase, $H_2O_2$-producing enzyme, oxidoredutase, expansin, swollenin, or a mixture thereof for example cellobiohydrolase I and/or II, endoglucanase I and/or II, and betaglucosidase activity. The complex containing the polypeptides with cellulase and/or hemicellulase activities, as well other polypeptides having at least one among the said activities is herein a "polypeptide complex."

The dosing of the polypeptide complex that must be added to the culture medium can range from 0.5% to 15% w/w (peptides/total solids), but the most preferable concentration is between 1% and 5% w/w.

The concentration of the polypeptide complex and its action time are important to degrade only partially the fiber pulp, but not degrade it completely. The partly degraded fiber pulp that remains solid in the medium allows the increase of surface area where the fermentative microbes will be immobilized.

Thereby, the culture medium for ABE fermentation described in the present process comprises the hydrolysate, fiber pulp and the polypeptide complex mixed in quantities and proportion as described previously.

The fifth step (5) of the present process concerns on the addition of the fermentative microbes into the culture medium. The microbe is a wild type, a mutant type or a genetically modified type selected from the group of Clostridium species, preferably C. acetobutylicum, C. beijerinckii, C. saccharoperbutylacetonicum, C. sacharobutylicum and C. pasteurianum; or the microbe is a microorganism selected to or genetically modified to produce solvents, preferably butanol.

The growth condition that optimizes biomass accumulation and production rate are the following: fermentation under anaerobic atmosphere, initial pH value between 4 and 8, preferably between 5.5 and 6.8, temperature between 20° C. and 40° C., preferably between 30° C. and 35° C., and initial cell concentration between an optical density (600 nm) 0.5 and 5, preferably between 1.5 and 3.

The sixth step (6) of the present process regards to the use of the culture medium and microbes (described from steps 1 to 5) to start a regular batch fermentation. It is important pointing that in the present process the cellulosic fiber pulp previously degraded by the action of the polypeptide complex works as matrix to allow the Clostridium immobilization, as previously stated.

Therefore, considering that the partly degraded fiber pulp itself is able to immobilize the Clostridium cells, no additional apparatus is necessary to support the immobilization matrix featuring a differential of the present process. In other words, the present process uses a mobile matrix for microbe immobilization and batch fermentation, avoiding the disadvantages related to the complexity of reactors design and to the constant maintenance and sterilization required by matrices current described in the state of the art.

Additionally, the batch fermentation made by using the previously described culture medium, which is supplemented with fiber pulp and polypeptide complex, which has cellulase and/or hemicellulase activity, allows not only the Clostridium immobilization, but also favors cell growth causing an increase of cell concentration. In this case, a reduced number of fermentation tanks will be necessary to reach high cell biomass concentration, because of better distribution of nutrients/space and avoiding competition between cells for the available resources.

The nutrients that are released in the culture medium by the partial degradation of the fiber pulp consists of monosaccharides, oligosaccharides, organic acids, phenolic compounds, salts and/or peptides from plant cellular components. These nutrients comprise components analogous to the autoinducers compounds, related to quorum sensing system, that are naturally released by bacteria cells and that starts the quorum sensing process.

In the present process, the nutrients analogous to the autoinducers are released into the medium in a constant and homogenous way during the partial fiber pulp degradation by the polypeptide complex. At the time these nutrients reach enough concentration, they start the bacterial quorum sensing phenomenon, activating genes responsible by the solventogenesis and allowing the increase of solvent production.

Both together, immobilization and quorum sensing, promote the improvement of the fermentation performance and solvent production by overcoming some of the main technical problems of ABE fermentation: the low productivity and low yield of solvents. The present invention also allows the solvent production process industrially efficient and easily scalable.

After solvent production the seventh (7) step of the present process comprises the optional separation and recovering of the produced solvent.

EXAMPLES

Example 1: Effect of Fiber Pulp Combined with Polypeptide Complex for Cell Immobilization and Increasing in Solvent Production The present experiment was performed with Clostridium saccharoperbutylacetonicum DSM 14923 obtained from DSMZ (German Collection of Microorganisms and Cell Cultures). Clostridial Nutrient Medium, CNM (e.g. Sigma Aldrich, that comprises 0.5 g/L of L-cysteine hydrochloride, 5 g/L of D(+)-glucose, 10 g/L of beef extract, 5 g/L de peptone, 3 g/L of sodium acetate, 5 g/L of sodium chloride, 1 g/L of starch, 3 g/L of yeast extract, 0.5 g/L of agar) was used for cell propagation and inoculum preparation.

Batch fermentations were performed in anaerobic chamber using filter sterilized hydrolysate. The present embodiment uses the hydrolysate from sugarcane straw, which comprise 35-50 g $L^{-1}$ of sugars, that may be preferentially supplemented with yeast extract, minerals, vitamins and adjusted to pH 6.8 with NaOH and, depending on the cultivation conditions as described forward, cellulases and hemicellulases complex (e.g. a polypeptide complex such as Cellic® CTEC3 from Novozymes, 3% of the total solids) and/or 20 g $L^{-1}$ (dry weight) of fiber pulp fragmented into 1-10 mm particles were added to culture medium.

For inoculum preparation, 1 mL from a culture of vegetative cells was inoculated in 50 mL of Clostridial Nutrient Medium CNM (e.g. from Sigma-Aldrich, as previously described) and grown for 20 h at 32° C. After 20 h, the actively growing culture was centrifuged and cells were recovered and used as inoculum for batch fermentation that was done under four different culture conditions: (1) Control, using only the hydrolysate as culture medium; (2) using the hydrolysate supplemented with fiber pulp; (3) using de hydrolysate supplemented with the polypeptide complex; and (4) using the hydrolysate supplemented with fiber pulp and the polypeptide complex. In all experiments, initial cell concentration was an OD600 of 2.

Batch fermentation was done in a 100 mL bottle containing 50 mL of hydrolysate medium and all cultures were incubated in anaerobic chamber at 32° C. without agitation or pH control. During the course of fermentation, 1 mL sample was collected regularly for analysis of cell growth, sugar consumption and metabolites production.

Cell biomass was calculated by measuring the absorbance at 600 nm in a spectrophotometer UV/visible (e.g. ULTROSPEC 2000 from Pharmacia Biotech) after appropriate dilution in water. For HPLC-RI analysis, the samples were filtered through a 0.2 μm filter (Millipore). Butyric acid, acetic acid, acetone, ethanol, butanol and sugars were determined by HPLC (e.g. Waters 600 Chromatograph), using an ion exclusion column (e.g. Aminex HPX-87H, from Bio-Rad). The operation temperature was 35° C. and 0.16 M $H_2SO_4$ was used as the mobile phase at a flow rate of 0.6 mL/min.

Figure 1B:
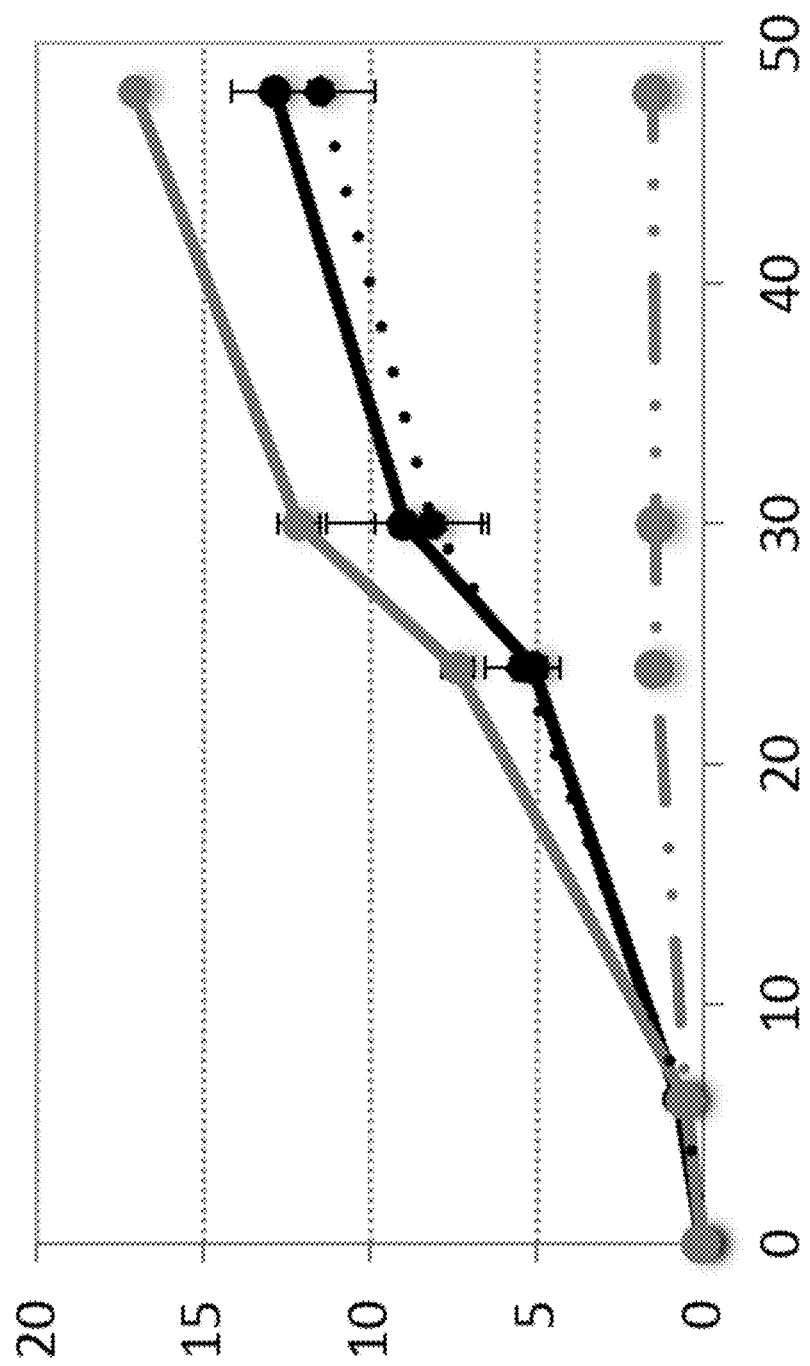
Figure 2A:
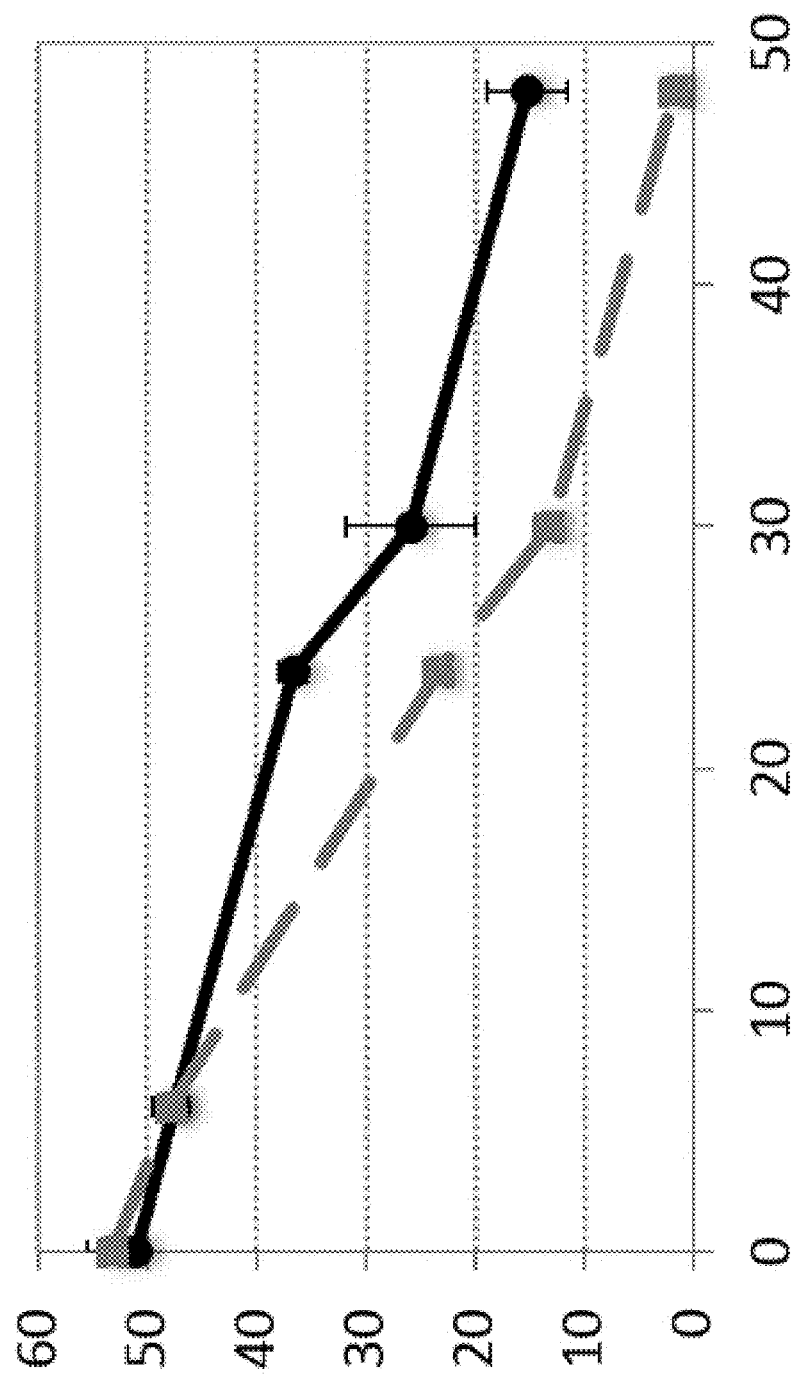
In FIGS. 2(*a*)-2(*d*), microbes were submitted to two different culture conditions: (1) Control, where the culture medium comprises only the hydrolysate ( ——— ); (2) pulp and the polypeptide complex were previously added to the hydrolysate, and acted together for 24 hours. After this time, the pulp was removed and the remaining liquid portion of the previous culture medium was used for microbe cultivation ( --- ).
Figure 2B:
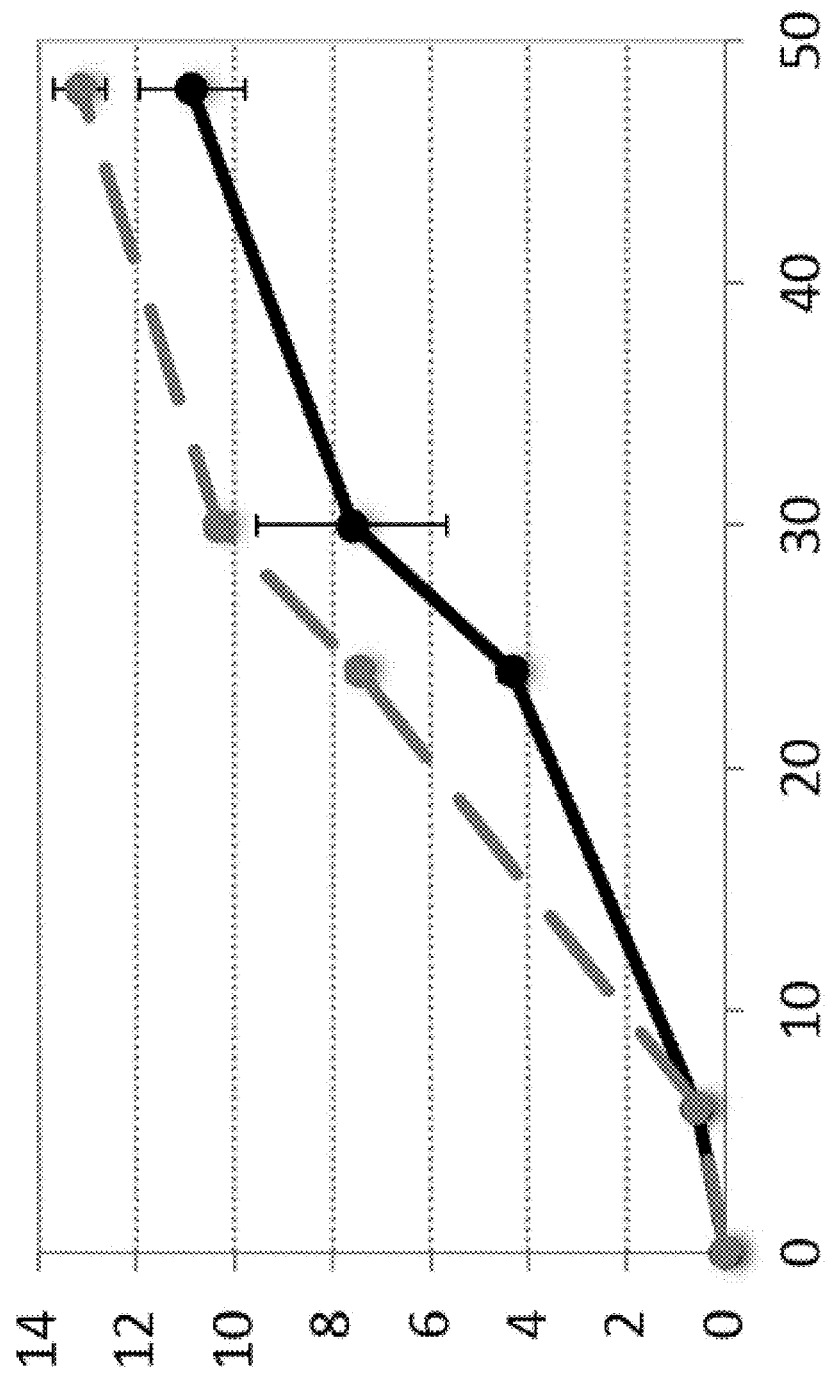
Figure 2C:
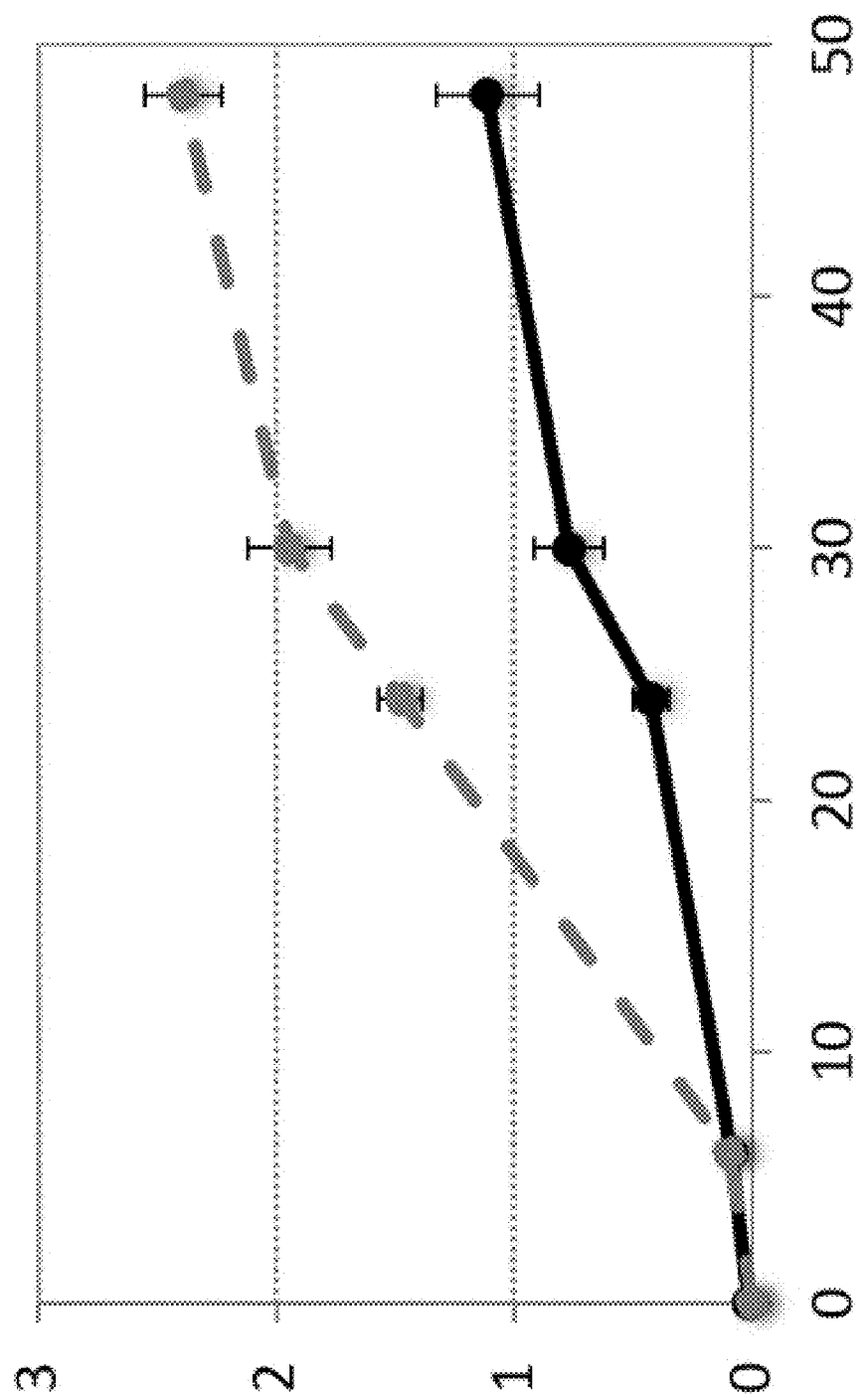
Figure 2D:
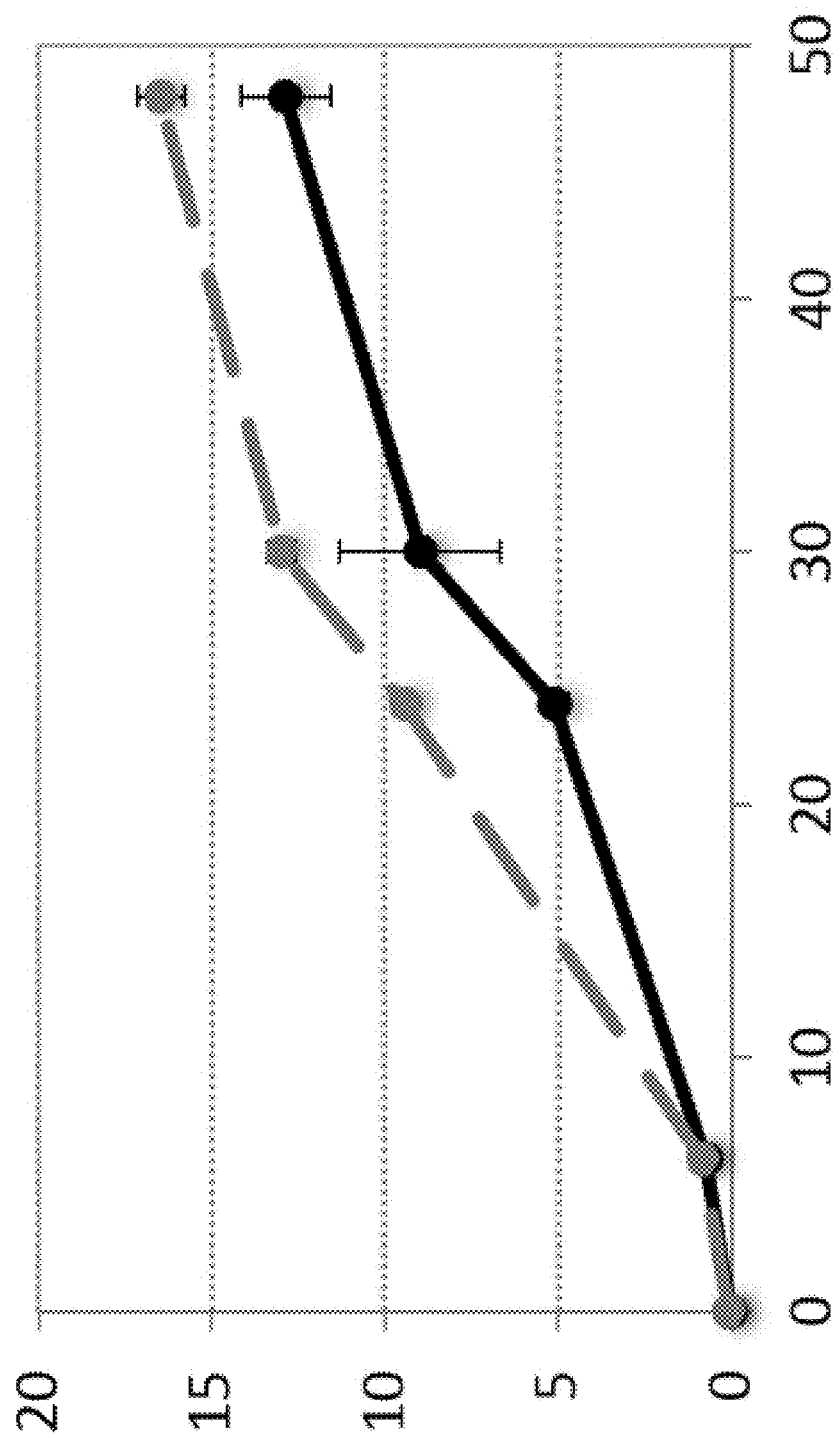
Figure 3A:
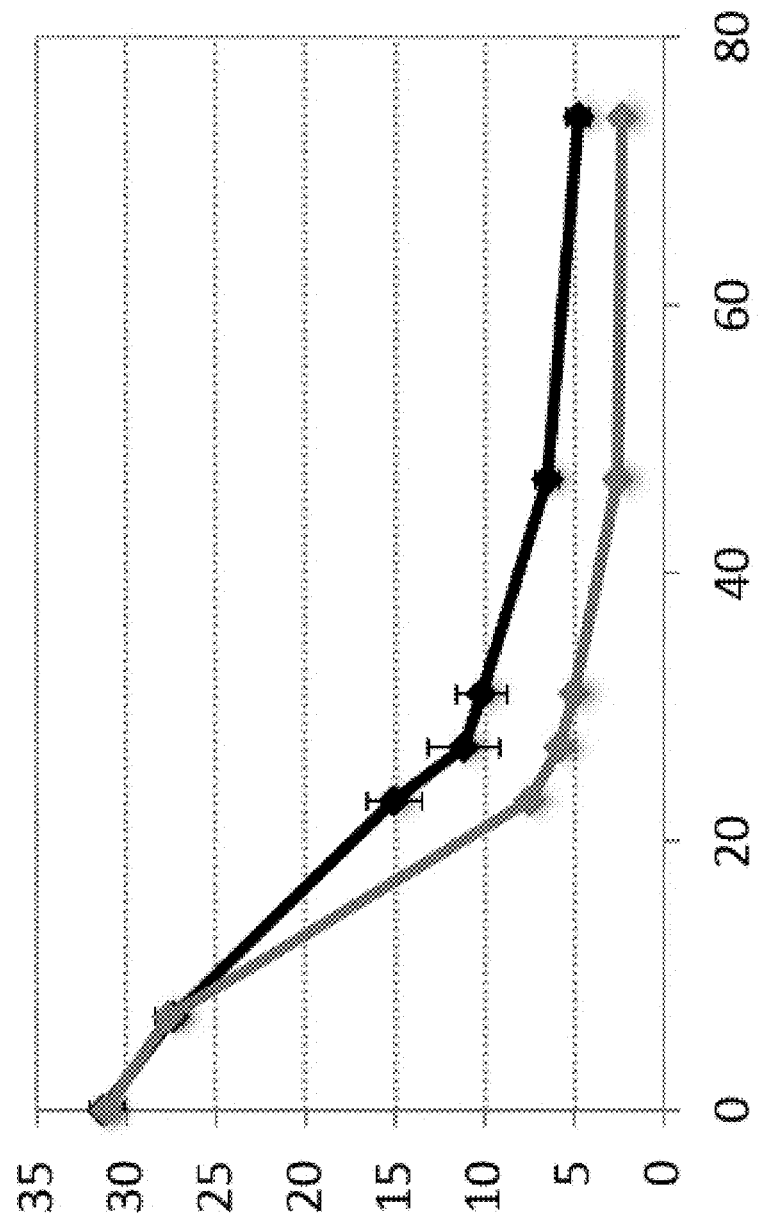
In FIGS. 3(*a*)-3(*d*), microbes were submitted to two different culture conditions: (1) Control, where the culture medium comprises only the hydrothermal hydrolysate obtained from sugarcane straw ( ——— ); (2) Hydrothermal hydrolysate supplemented with Aspen pulp and the polypeptide complex ( ▬▬▬ ).
Figure 3B:
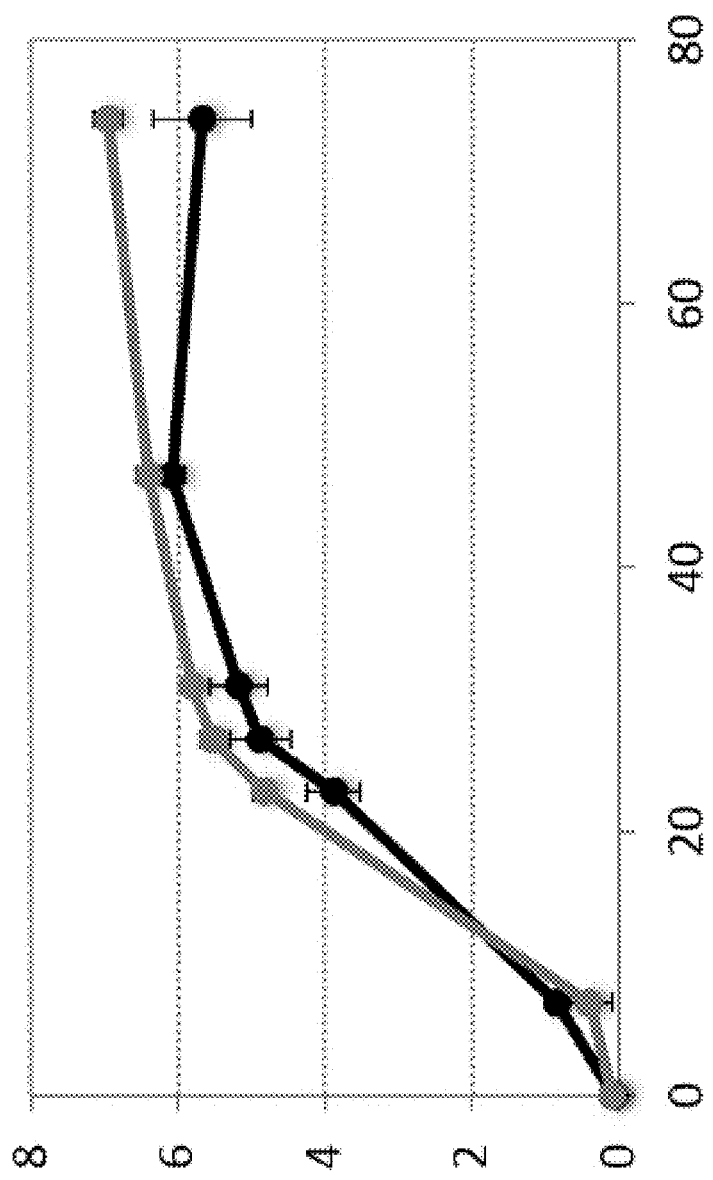
Figure 3C:
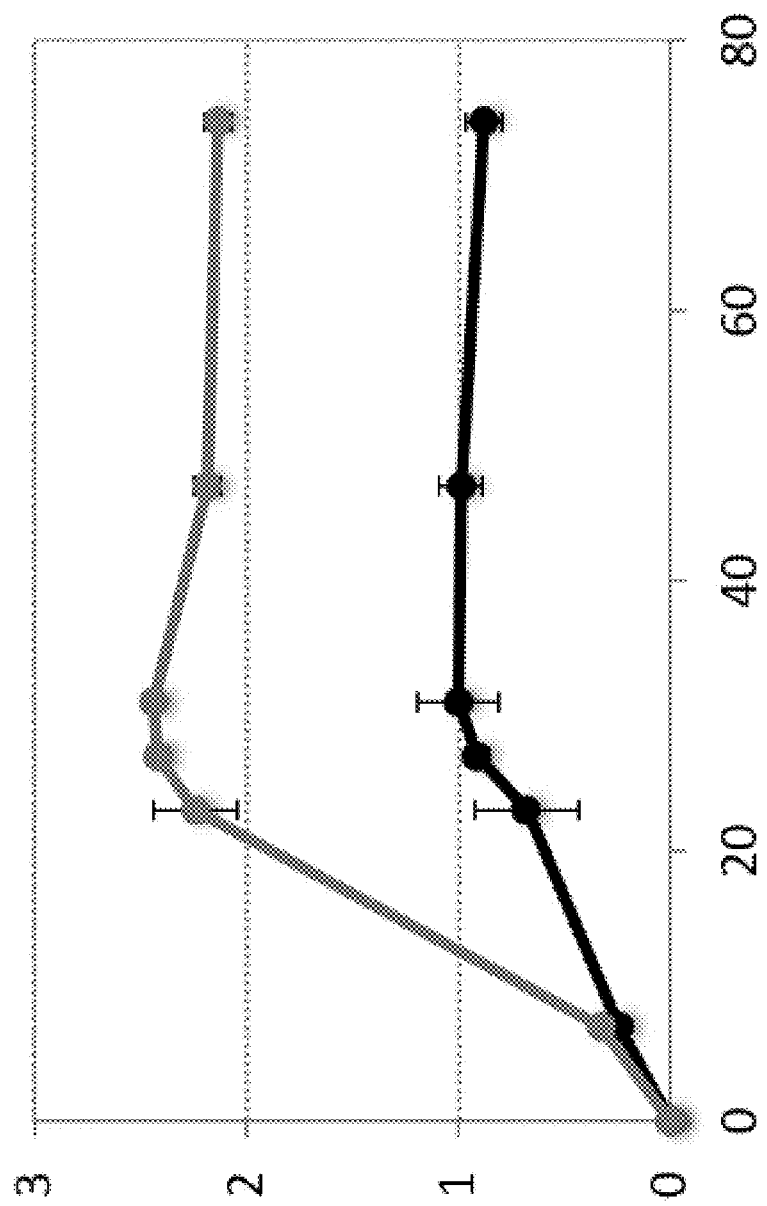
Figure 3D:
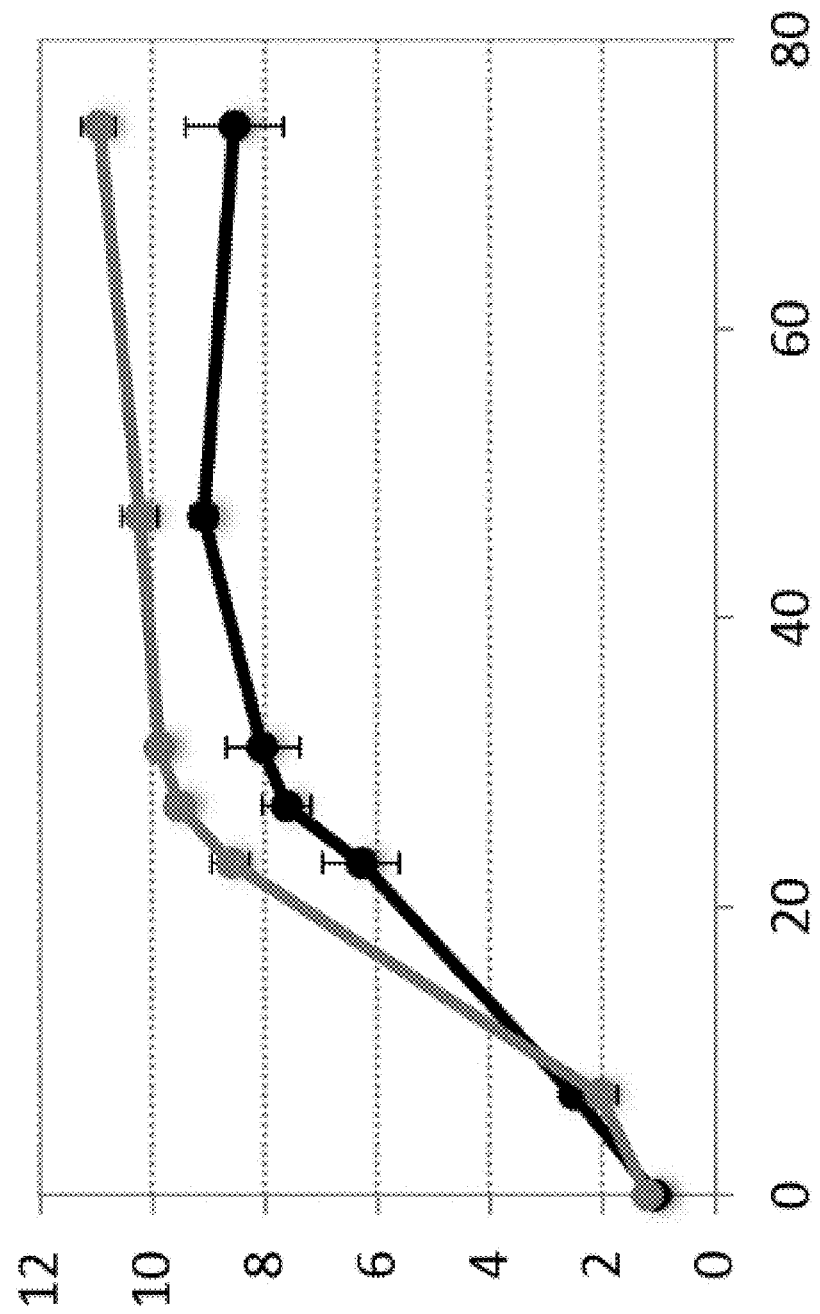
Figure 4A:
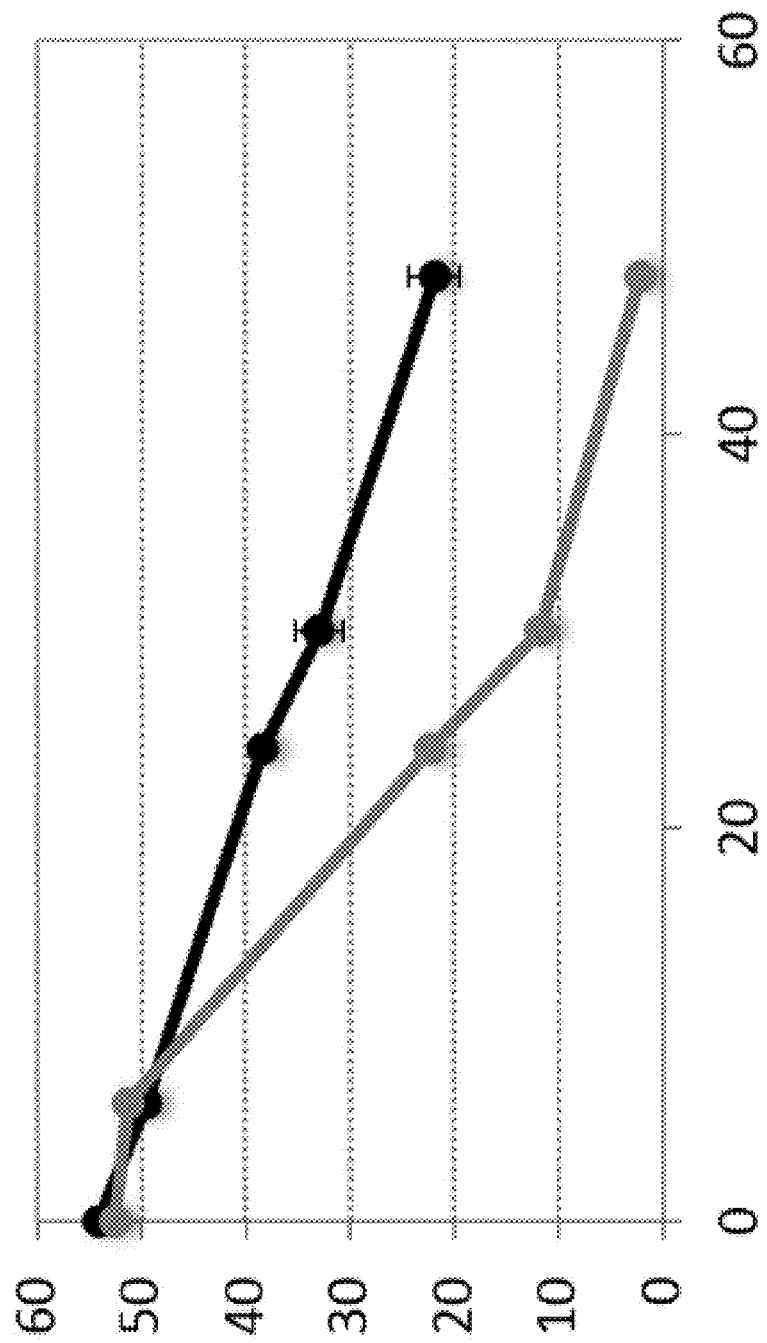
In FIGS. 4(*a*)-4(*d*), microbes were submitted to two different culture conditions: (1) Control, where the culture medium comprises only the hydrolysate obtained from cellulosic fiber pulp from sugarcane straw ( ——— ); and (2) Hydrolysate obtained from cellulosic fiber pulp from sugarcane straw supplemented with sugarcane pulp and the polypeptide complex ( ▬▬▬ ) In FIG. 4(*a*) it is possible to observe the sugar consumption (g/L), represented in the vertical axis, while time (h) is represented in the horizontal axis.
Figure 4B:
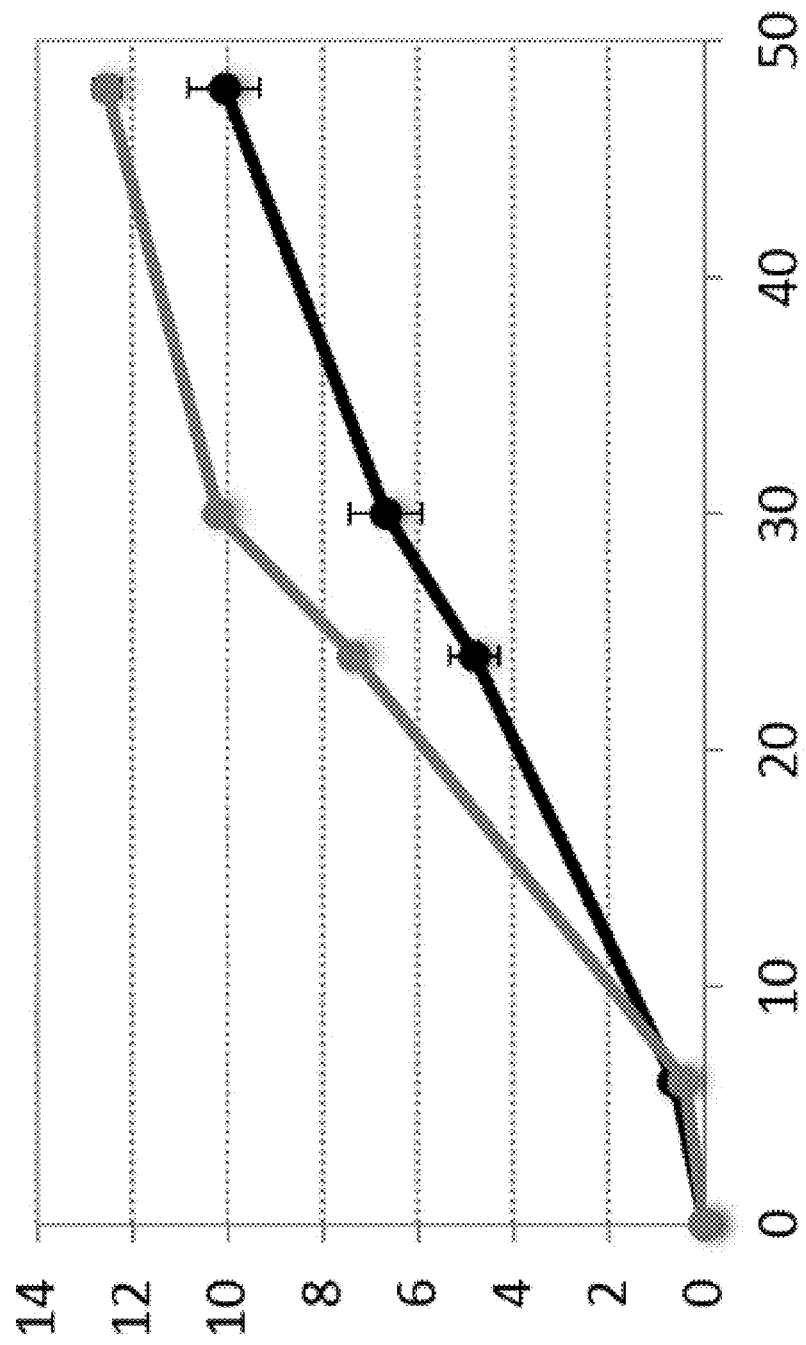
Figure 4C:
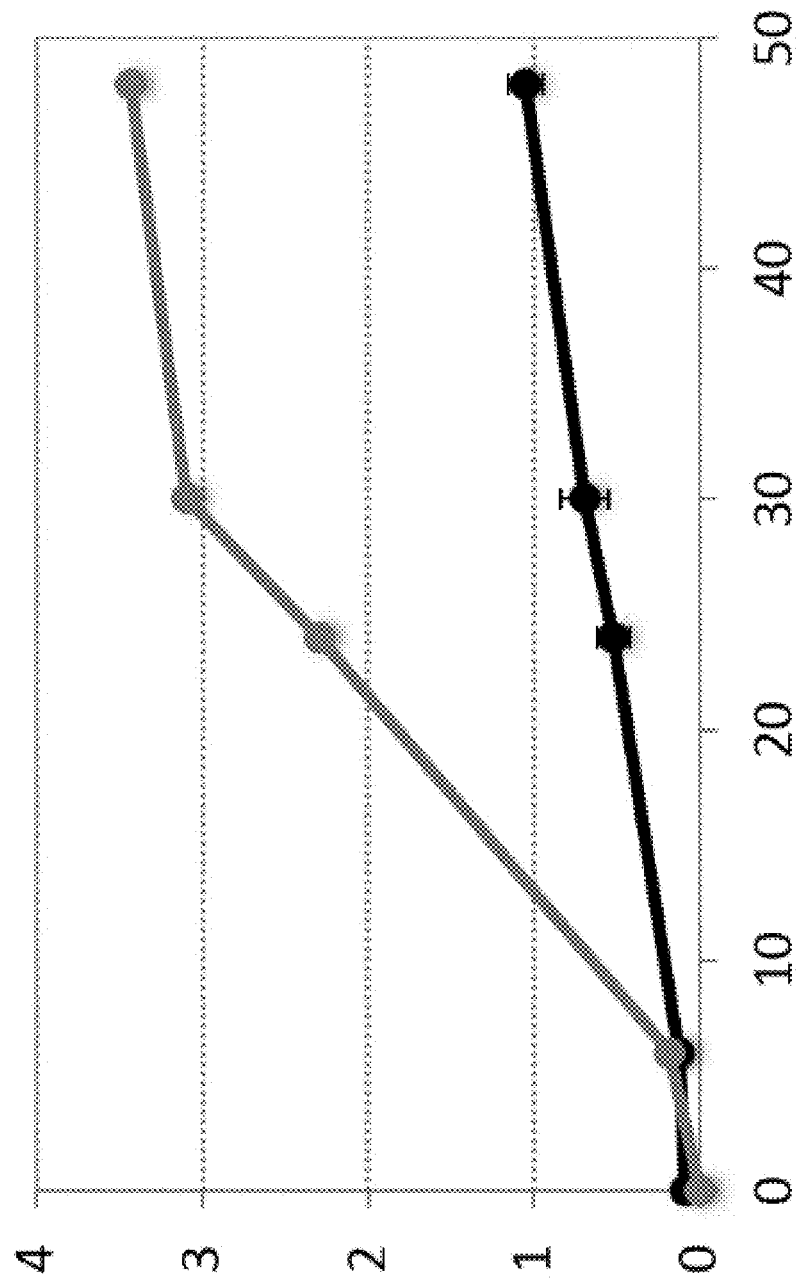
Figure 4D:
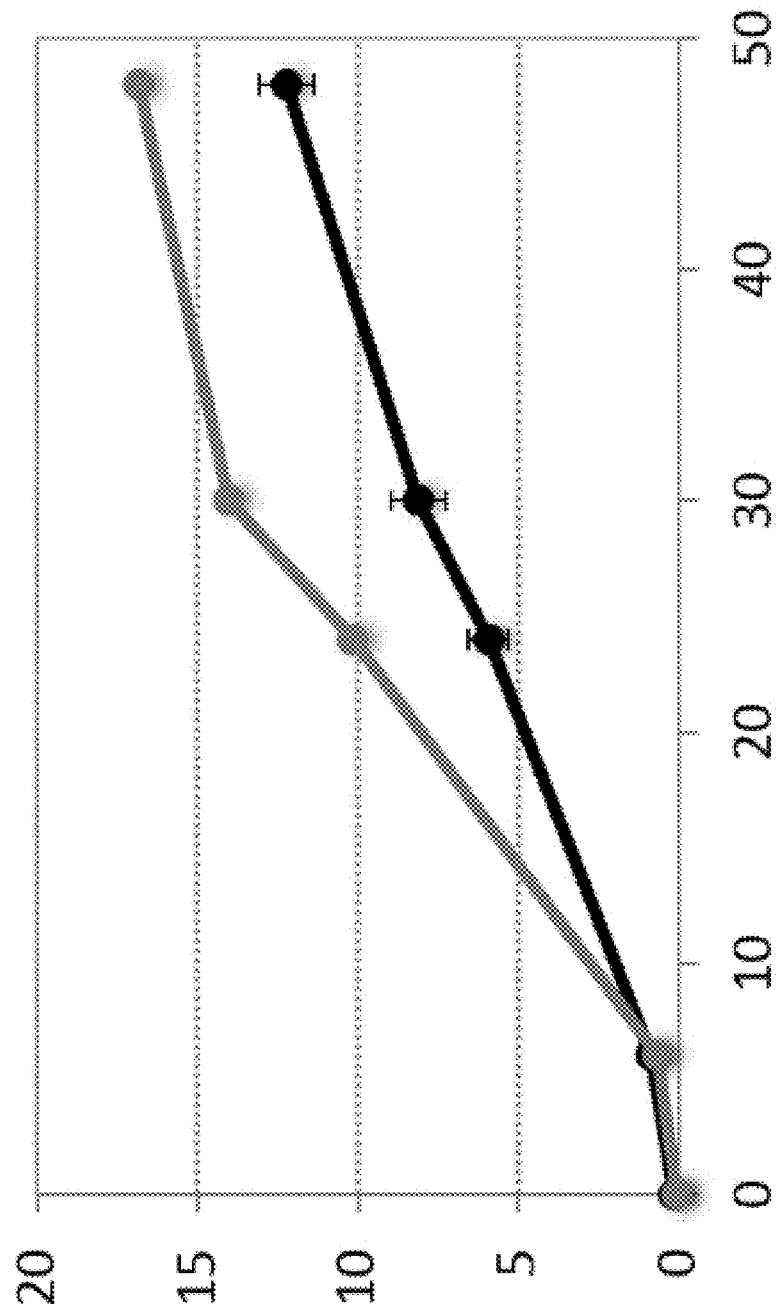

In FIGS. 1(a)-1(b) it is possible to observe faster sugar consumption and increased solvent production in the present process that uses the combination of lignocellulose hydrolysate, fiber pulp and polypeptide complex. The total solvent concentration and yield of 17.10 g $L^{-1}$ and 34.7% respectively, were achieved using the hydrolysate supplemented with fiber pulp and the polypeptide complex. These numbers represent an improvement of 32.8% in solvents concentration and 38% in solvents yield when compared to Control. Furthermore, the solvent production rate and the sugar consumption rate increased and a smaller amount of residual sugar was observed hydrolysate supplemented with fiber pulp and the polypeptide complex.

However, when a batch fermentation is done using the hydrolysate alone or the hydrolysate supplemented only with fiber pulp, or the hydrolysate supplemented only with the polypeptide complex, it is not possible to achieve the same improvements achieved using hydrolysate supplemented with the fiber pulp together with the polypeptide complex. Therefore, it is observed that the fiber pulp together with the polypeptide complex are preferred for cell immobilization, which confers more tolerance to toxic compounds, as solvents, allowing greater cell growth and the larger production of solvents, as acetone and butanol.

Example 2: Effect of Cellulosic Fiber Pulp and Enzyme Complex on ABE Fermentation After Removal of the Pulp These experiments were performed according to methods described in Example 1, except for the modifications described forward. Batch fermentation was performed using hydrolysate, e.g, from sugarcane straw, under two different situations: (1) Control, using only the hydrolysate and (2) using the hydrolysate supplemented with the polypeptide complex and fiber pulp just after the pulp removal. More specifically, in this situation (2), before cell inoculation, fiber pulp and the polypeptide complex were added to culture medium, and it was incubated for 24 hours. Then, the medium was centrifuged to remove the pulp (solid portion) and the remainder liquid portion of the medium was recovery and used as the culture medium for bacteria inoculation. FIGS. 2(a)-2(d) show the results of sugar consumption and metabolites production.

The total solvent concentration and yield were also improved even when fiber pulp was removed. Indeed we reported an increase of 22.7% and 28% in solvent yield and productivity, respectively, when compared to Control. The fermentation performance improvement is related with digested pulp removal indicating that during the hydrolysis of the fiber pulp some compound responsible for enhancing of ABE fermentation performance is release from fiber pulp and not only the cell immobilization is related to ABE fermentation improvement.

It is important to consider that when the polypeptide complex alone is added to the hydrolysate no result is observed in respect of the ABE fermentation performance, as previously shown, proving that the polypeptide complex alone have no effect in solvent production.

Based on previous report about quorum sensing system (US 2015/0031102 A1 and Kosaka et al., 2007) it is possible to find out that under these hydrolysis conditions (32° C. and pH 6.8) a quorum sensing inducer compound is released from the fiber pulp and it is responsible for coordinating gene expression related to solvent production. Besides, through the analysis of acetone production (FIG. 2(c)) we can notice a lower titer of acetone in removed pulp experiment compared to batch fermentation with fiber pulp and the polypeptide complex. Under this context, there is a solvent production improvement as consequence of quorum sensing gene expression and cell immobilization on fiber pulp.

Example 3: Effect of Cellulosic Fiber Pulp from Aspen Wood and Enzyme Complex on ABE Fermentation Using Hydrothermal Hydrolysate Based on the methods previously described, a set of experiments were carried out to demonstrate the effect of fiber pulp and polypeptide complex on ABE fermentation using hydrothermal hydrolysate from sugarcane straw, instead of the hydrolysate obtained by the organosolv process. Due to great amount of toxic compounds present in this hydrothermal hydrolysate, only 30 g $L^{-1}$ of total sugars was available in the culture medium instead of the 50 g $L^{-1}$ described in Example 1.

Corroborating the results reported on Example 1, the solvent titer and yield were also improved by the present process, showing that it is viable even when using a different kind of hydrolysate supplemented with fiber pulp and polypeptide complex (FIGS. 4(a)-4(d)). In this case, the total solvent concentration and yield of 11 g $L^{-1}$ and 35%, respectively, were achieved using the fiber pulp and polypeptide complex. These numbers represent an improvement of 28% in solvents concentration and 29% in solvents yield when compared to control. Furthermore, the solvent production rate and the sugar consumption rate increased, and a smaller amount of residual sugar was observed using cellulosic fibers.

Figure 5A:
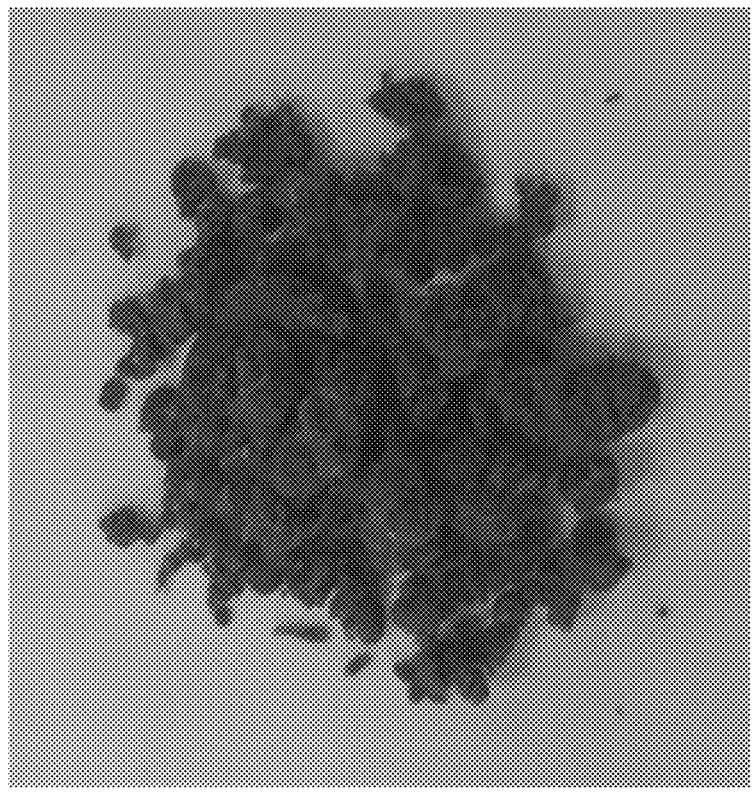
In FIGS. 5(*a*) and 5(*b*) it is possible to observe the cellulosic fiber pulps from (a) sugarcane straw and (b) Aspen wood.
Figure 5B:

Example 4: Effect of Fiber Pulp from Sugarcane Straw and Polypeptide Complex on ABE Fermentation Using the Hydrolysate Obtained from the Fiber Pulp In order to demonstrate that fermentation performance can be increased using different types of fiber pulp and the results described above is not related only to fiber pulp from Aspen wood, a set of batch fermentations was also carried out with fiber pulp from sugarcane straw. Both pulps were obtained using the same biomass pretreatment however, they have different characteristics. The sugarcane straw pulp is a dark brown material and has a large amount of silica and a soil aspect, while the Aspen wood pulp is a beige color material and has a paperboard aspect (FIGS. 5(a)-5(b)). The experiments were performed in the same conditions as described in Example 1 and the results are represented in FIGS. 4(a)-4(d).

As reported previously for Aspen wood pulp, the solvent production was improved in a batch fermentation supplemented with fiber pulp from sugarcane and the polypeptide complex. Under these conditions, the solvent titer and yield increased 37.7% and 42%, respectively, when compared to control, showing the viability of the present process in the improvement of solvent production.

Example 5: Effect of Different Concentrations of Fiber Pulp from Sugarcane Straw and Polypeptide Complex on ABE Fermentation The fermentation performance can be improved even using small concentrations of fiber pulp. In order to demonstrate this improvement an experiment was performed according to the methods described in Example 1, except for the amounts of fiber pulp supplemented in culture medium, which were 0 g/L (control), 5 g/L, 10 g/L, 20 g/L and 30 g/L. In addition, cellulases and hemicellulases complex was added at concentration of 3% of total solids.

Figure 6A:
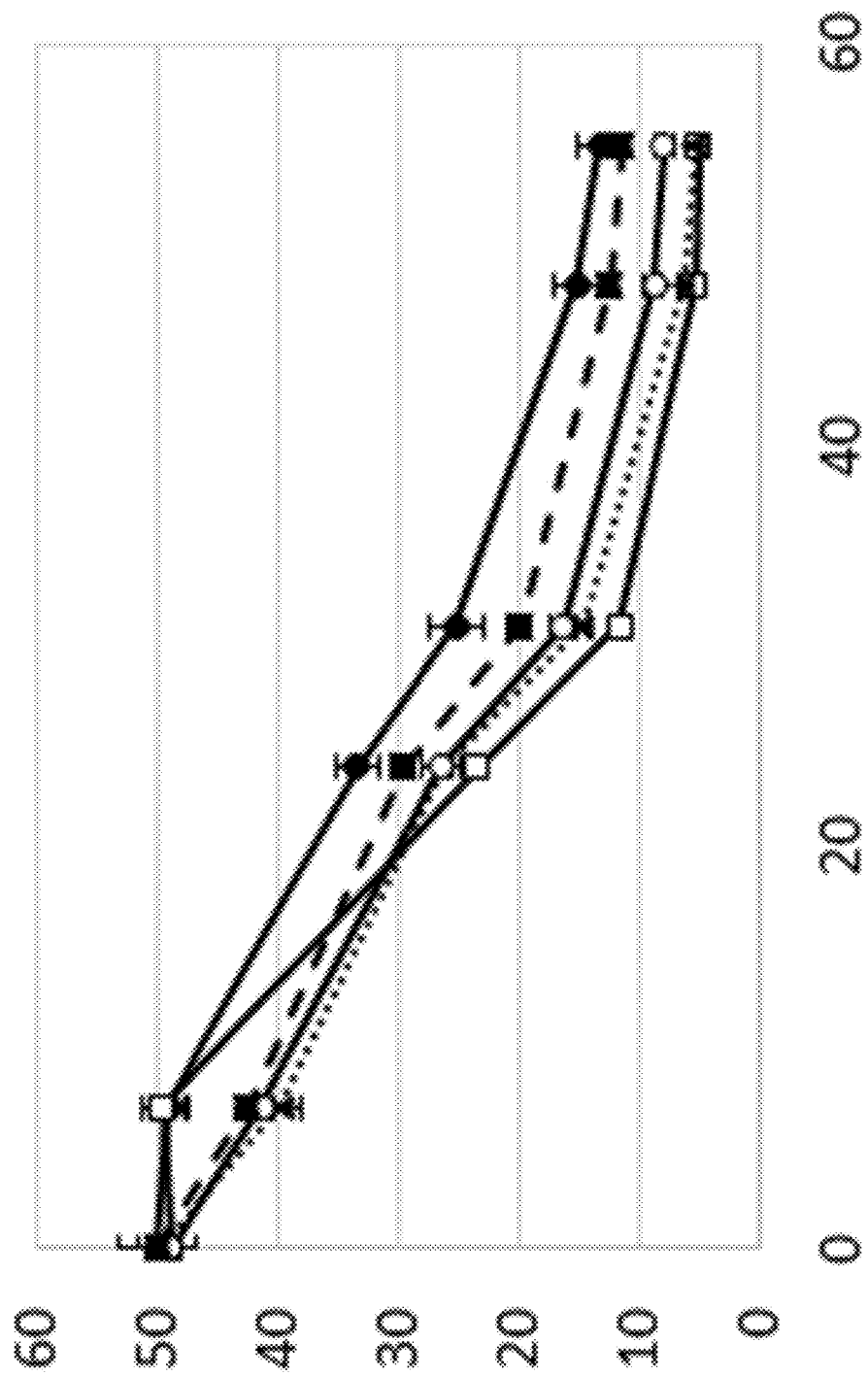
In FIG. 6(a), it is possible to observe the total sugar consumption (g/L), represented in the vertical axis, while time (h) is represented in the horizontal axis.

We observed that the amount of residual sugar in the culture medium was proportional to the amount fiber pulp that was added to the medium, in other words, the residual sugar was greater when the culture medium was supplemented with large amounts of fiber pulp, as observed in FIG. 6(a).

Figure 6B:
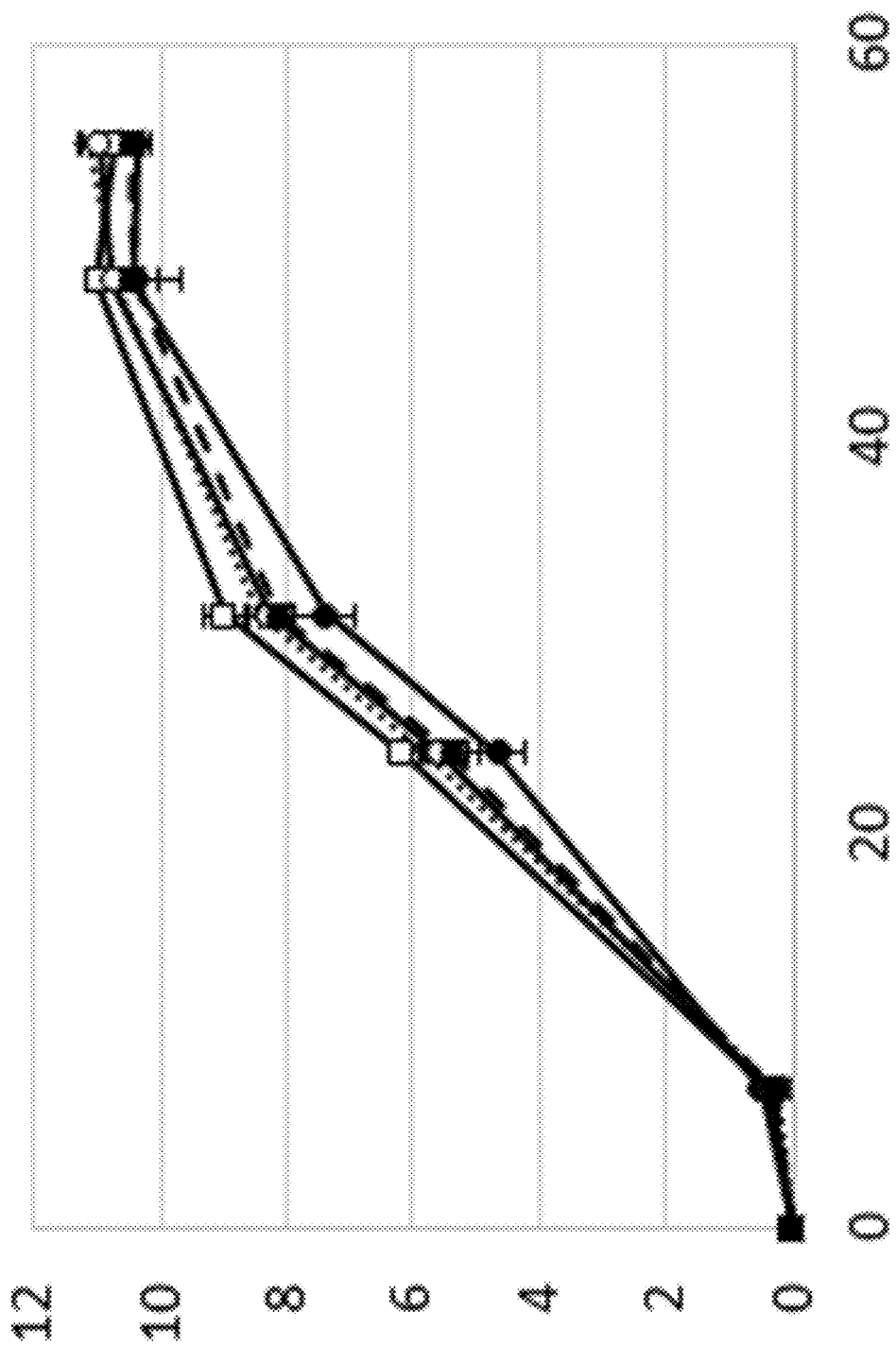
In FIG. 6(b), is possible to observe the butanol production (g/L) in the vertical axis, by time (h) in the horizontal axis.
Figure 6C:
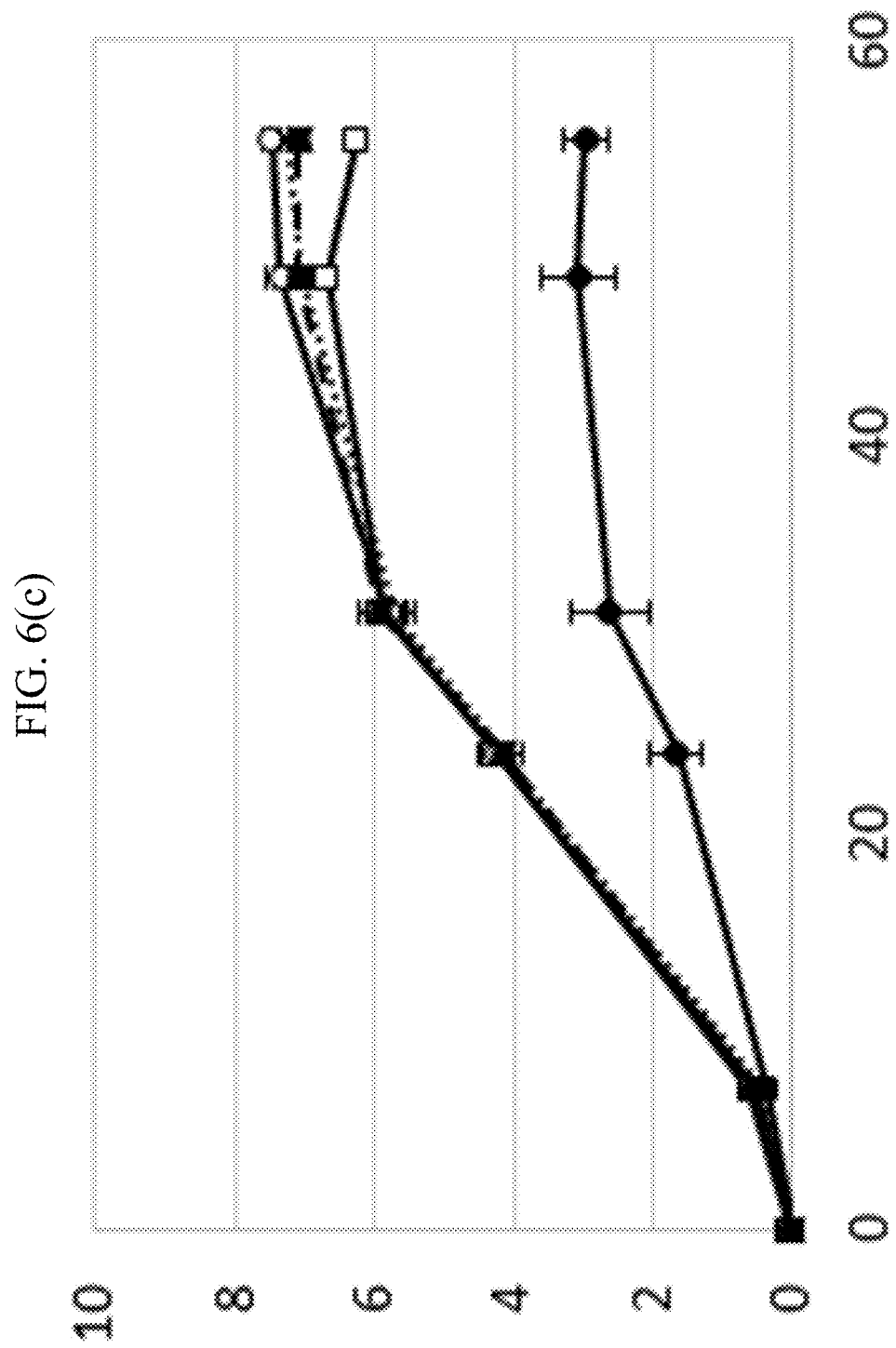
In FIG. 6(c), it is possible to observe the acetone production (g/L), represented in the vertical axis, while time (h) is represented in the vertical axis. In the FIG. 6(d), it is possible to observe the total solvent production (g/L) represented in the vertical axis, while time (h) is represented in the horizontal axis.
Figure 6D:
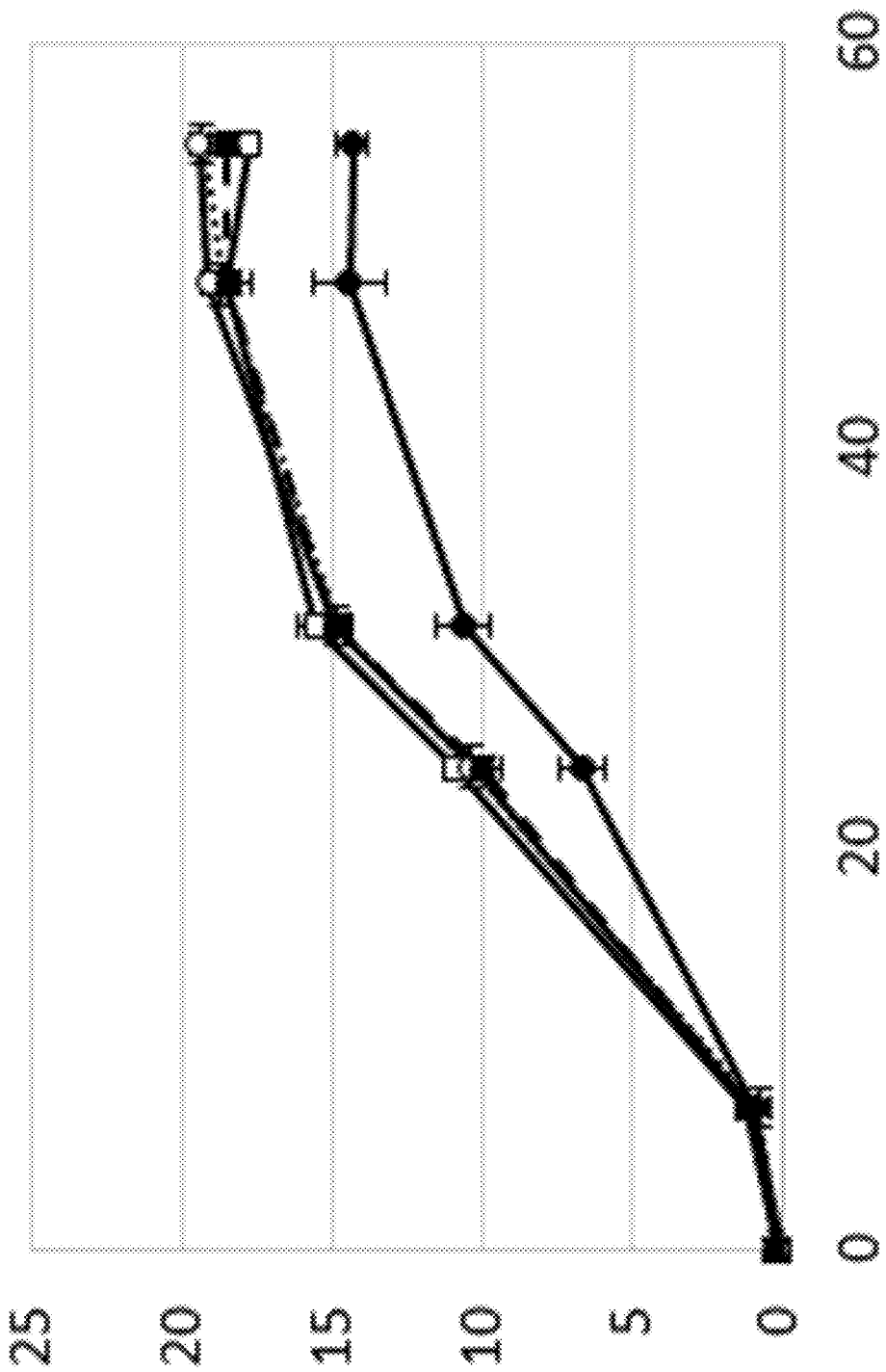
In FIGS. 6(*a*)-6(*d*) microbes were cultivated in 5 different conditions. (1) Control, where the culture medium comprises only the hydrolysate ( –●– ); (2) hydrolysate supplemented with 5 g/L of pulp and polypeptide complex ( –□– ); (3) hydrolysate supplemented with 10 g/L of pulp and polypeptide complex ( –▲– ); (4) hydrolysate supplemented with 20 g/L of pulp and polypeptide complex ( –○– ) and (5) hydrolysate supplemented with 30 g/L of pulp and polypeptide complex (-■-).

However, the solvent production and titer were increased in all the supplementations of fiber pulp (5 g/L, 10 g/L, 20 g/L and 30 g/L), when compared to the Control (0 g/L) and similar numbers were achieved in all the supplementations, as observed in the FIGS. 6(b), (c) and (d). This result indicates that the other substances that are released in small quantities from the fiber pulp, which allows the beginning of the quorum sensing phenomenon, together with the cell immobilization, that is also allowed by the fiber pulp, that makes the present invention advantageous.

Therefore, this result supports the principle of the present invention, demonstrating that the combination of the substances released in small quantities by the pulp, together with the cell immobilization, improves solvent production.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

The claims herein are intended to describe embodiments of the invention and shall be construed as forming a part of the written description and specification.

What is claimed is:

1. A process for converting lignocellulosic biomass into fermentation products, the process comprising: (1) submitting the lignocellulosic material to a pulping process, to obtain pulp; (2) submitting additional lignocellulosic biomass and/or fiber pulp to a hydrolysis process, to obtain hydrolysate; (3) mixing the pulp from step (1) with the hydrolysate, to obtain a culture medium; (4) adding a polypeptide complex into the culture medium; (5) adding a fermentative microbe into the culture medium, to obtain a fermentation medium; (6) fermenting the fermentation medium to produce fermentation products; and (7) recovering the fermentation products, wherein total free sugar concentration in the hydrolysate obtained in step (2) is at least 20 grams (g) of sugar per liter (L) of hydrolysate, and wherein an amount of fiber pulp added to the culture medium in step (3) is at least 2 to 20 times smaller (in g/L) than the total free sugar concentration available in the culture medium (in g/L).

2. The process according to claim 1, wherein the lignocellulosic material described in steps (1) and (2) comprises lignocellulosic material naturally found as a component of algae or plant cell wall.

3. The process according to claim 1, wherein the lignocellulosic material described in steps (1) and (2) comprises wood cellulose obtained from agriculture crop residues or derivatives.

4. The process according to claim 1, wherein the pulping process described in step (1) comprises ethanol-water-sulfur dioxide fractionation, organosolv treatment, kraft, stone groundwood, mechanical refiner, thermomechanical pulping, defibrated or exploded pulping, and/or recycled paper processing.

5. The process according to claim 1, wherein the pulping process described in step (1) comprise treatment in the presence of an acid catalyst, a solvent for lignin, and water.

6. The process according to claim 1, wherein lignocellulosic biomass remains solid after the pulping process described in step (1).

7. The process according to claim 1, wherein the fiber pulp described in step (2) is obtained in step (1).

8. The process according to claim 1, wherein the hydrolysis process described in step (2) comprises enzymatic hydrolysis, acid hydrolysis, or hydrothermal hydrolysis.

9. The process according to claim 1, wherein step (3) results in a solid-liquid mixed blend.

10. The process according to claim 1, wherein an amount of hydrolysate that is added in step (3) is selected based on the total free sugar concentration in the hydrolysate.

11. The process according to claim 1, wherein the polypeptide complex described in step (4) comprise polypeptides that have mostly cellulase and/or hemicellulase activities.

12. The process according to claim 11, wherein the polypeptide complex described in step (4) comprises polypeptides that have at least one of the following activities: cellulolytic and/or xylanase, beta-xylosidase, carbohydrate-estarase, pectinase, protease, catalase, laccase, peroxidase, $H_2O_2$-producing enzyme, oxidoredutase, expansin, swollenin, cellobiohydrolase I and/or II, endoglucanase I and/or II, betaglucosidase, or a combination thereof.

13. The process according to claim 11, wherein the polypeptide complex described in step (4) added to the culture medium ranges from 0.5% to 15% w/w (peptides/total solids).

14. The process according to claim 1, wherein the fermentative microbe described in step (5) is a wild type, a mutant type or a genetically modified type selected from the group of *Clostridium* species or a microorganism selected to, or genetically modified to, produce solvents.

15. The process according to claim 14, wherein the fermentative microbe described in step (5) is *C. acetobutylicum, C. beijerinckii, C. saccharoperbutylacetonicum, C. sacharobutylicum* or *C. pasteurianum*.

16. The process according to claim 14, wherein the fermentative microbe described in step (5) is a microorganism selected to, or genetically modified to, produce butanol.

17. The process according to claim 1, wherein the fermentative products obtained are acetone, n-butanol and ethanol.

* * * * *